United States Patent
Kagawa et al.

(10) Patent No.: US 9,618,726 B2
(45) Date of Patent: Apr. 11, 2017

(54) ENDOSCOPE APPARATUS

(71) Applicant: OLYMPUS CORPORATION, Tokyo (JP)

(72) Inventors: Hiroaki Kagawa, Sagamihara (JP); Hironobu Ichimura, Akishima (JP); Kenji Omachi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 67 days.

(21) Appl. No.: 14/702,095

(22) Filed: May 1, 2015

(65) Prior Publication Data
US 2015/0309284 A1     Oct. 29, 2015

Related U.S. Application Data

(63) Continuation of application No. PCT/JP2014/058754, filed on Mar. 27, 2014.

(30) Foreign Application Priority Data

Apr. 19, 2013 (JP) .................................. 2013-088724

(51) Int. Cl.
*G02B 13/00* (2006.01)
*A61B 1/00* (2006.01)
(Continued)

(52) U.S. Cl.
CPC ............ *G02B 13/0015* (2013.01); *A61B 1/00* (2013.01); *A61B 1/00163* (2013.01); *A61B 1/04* (2013.01);
(Continued)

(58) Field of Classification Search
CPC ......... A61B 1/00; A61B 1/00163; A61B 1/04; A61B 1/05; G02B 13/0015; G02B 23/2415;
(Continued)

(56) References Cited

U.S. PATENT DOCUMENTS 5,191,203 A * 3/1993 McKinley .......... A61B 1/00193
                                                    250/208.1
5,701,520 A * 12/1997 Ishiguro ................. G03B 13/32
                                                    396/131
(Continued)

FOREIGN PATENT DOCUMENTS

JP     03-024512 A    2/1991
JP     11-197097 A    7/1999
(Continued)

OTHER PUBLICATIONS

International Search Report dated Apr. 28, 2014 issued in PCT/JP2014/058754.

*Primary Examiner* — Peter D Le
(74) *Attorney, Agent, or Firm* — Scully, Scott, Murphy & Presser, PC

(57) ABSTRACT

An endoscope apparatus includes an image pickup unit comprising a plurality of image pickup devices and an optical path dividing member for dividing an entering light beam into a plurality of optical paths, wherein respective optical path lengths are different from one another; a contrast comparing member for comparing contrasts of a plurality of images; an image selecting member for selecting and outputting only one image signal from one image pickup device among the plurality of image pickup devices, on a basis of comparison result by the contrast comparing member; and a driving member for moving a movable lens so that a difference among the contrasts of the plurality of images is largest, wherein a part of an objective lens is configured to be movable in an optical axis direction.

4 Claims, 13 Drawing Sheets

(51) Int. Cl.
*A61B 1/05* (2006.01)
*G02B 23/24* (2006.01)
*A61B 1/04* (2006.01)
*G02B 27/10* (2006.01)
*G02B 27/12* (2006.01)
*H04N 5/225* (2006.01)
*H04N 7/18* (2006.01)

(52) U.S. Cl.
CPC ............ *A61B 1/05* (2013.01); *G02B 23/2415* (2013.01); *G02B 23/2423* (2013.01); *G02B 23/2453* (2013.01); *G02B 27/1066* (2013.01); *G02B 27/126* (2013.01); *H04N 5/2254* (2013.01); *H04N 7/18* (2013.01)

(58) Field of Classification Search
CPC ............ G02B 23/2423; G02B 23/2453; G02B 27/1066; G02B 27/126; H04N 5/2254; H04N 7/18
See application file for complete search history.

(56) References Cited

U.S. PATENT DOCUMENTS 6,104,426 A * 8/2000 Street ................. G02B 23/2415
  348/45

2004/0027450 A1* 2/2004 Yoshino ............. H04N 13/0495
  348/42
2004/0057712 A1* 3/2004 Sato .......................... G03B 3/00
  396/89
2005/0013602 A1* 1/2005 Ogawa .................... G03B 15/05
  396/157
2007/0203394 A1* 8/2007 Wiklof ............... A61B 1/00188
  600/109
2008/0007716 A1* 1/2008 Igarashi .................... G01J 3/02
  356/72
2012/0105612 A1 5/2012 Yoshino
2013/0182173 A1* 7/2013 Murata ............. H01L 27/14605
  348/349

FOREIGN PATENT DOCUMENTS

| | | |
|---|---|---|
| JP | 2007-050106 | 3/2007 |
| JP | 4955840 B2 | 3/2012 |
| JP | 2012-095828 A | 5/2012 |
| JP | 2012-110481 A | 6/2012 |
| JP | 2013-022262 A | 2/2013 |
| WO | WO 2013/027459 A1 | 2/2013 |
| WO | WO 2013/061819 A1 | 5/2013 |

* cited by examiner (A)　　　　　　　　　　(B)

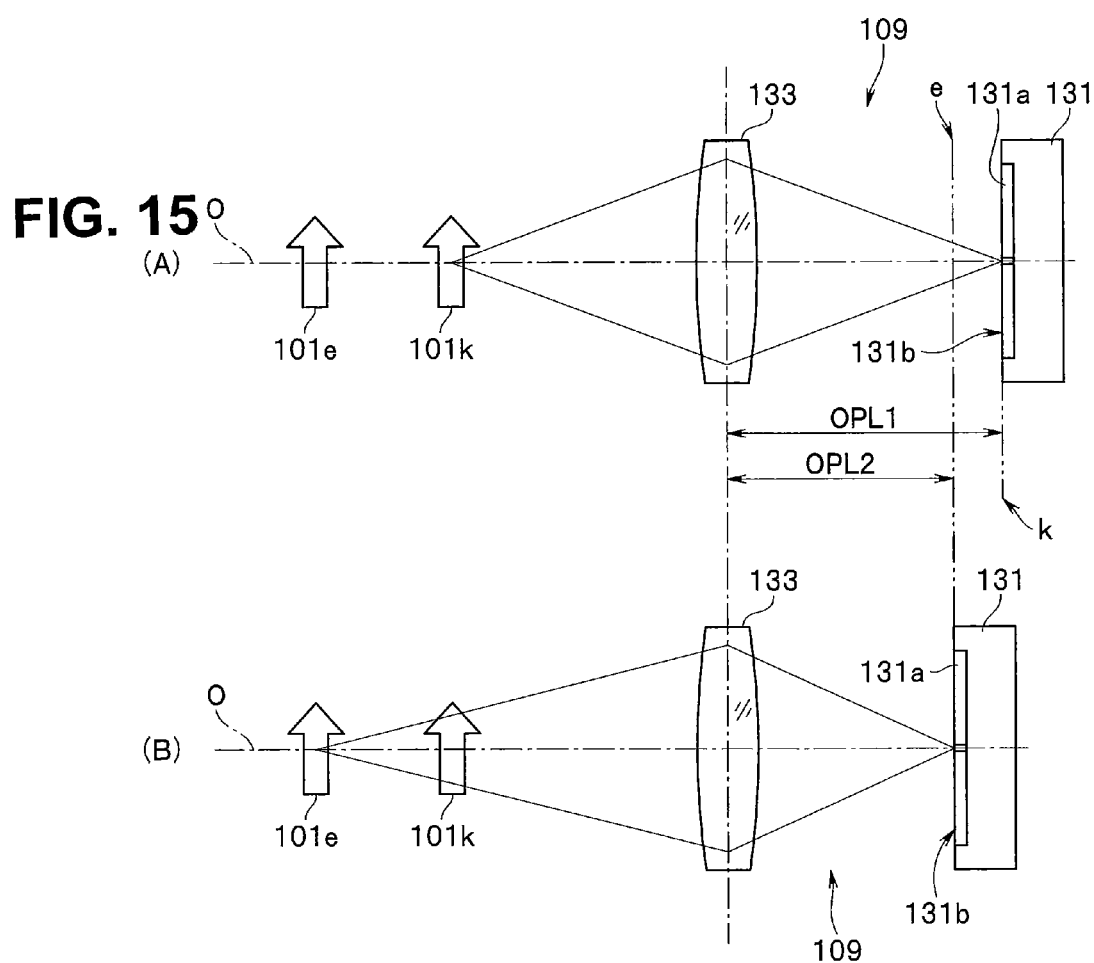

ENDOSCOPE APPARATUS

CROSS REFERENCE TO RELATED APPLICATION

This application is a continuation application of PCT/JP2014/058754 filed on Mar. 27, 2014 and claims benefit of Japanese Application No. 2013-088724 filed in Japan on Apr. 19, 2013, the entire contents of which are incorporated herein by this reference.

BACKGROUND OF THE INVENTION

1. Field of the Invention

The present invention relates to an electronic endoscope apparatus which performs photoelectric conversion of an optical image formed by an image pickup optical system with an image pickup device to output an electronic image signal.

2. Description of the Related Art

Recently, in a medical field or an industrial field, an electronic endoscope apparatus has been widely and generally put to practical use which is provided with an image pickup unit constituted by an image pickup optical system, an image pickup device and the like, at a distal end portion of an elongated insertion portion, and configured to be capable of displaying an image of a subject on a display device and observing the image by performing photoelectric conversion of an optical image formed by the image pickup optical system with the image pickup devices and outputting an electronic image signal to the display device. An endoscope apparatus for the medical field is configured such that observation and the like inside a body cavity can be performed by inserting the insertion portion into a body from an oral cavity, an anus or the like. Further, an endoscope apparatus for the industrial field is configured such that internal observation and the like can be performed by inserting the insertion portion into a pipework of plant facilities, such as a boiler, an inside of an engine or the like.

There is a remarkable tendency that the number of pixels of an image pickup device adopted for an endoscope apparatus of this kind is increased for the purpose of improving image quality and resolution of an acquired image. Therefore, it becomes possible to improve resolution and obtain a high-quality image by increase in the number of pixels of an image pickup device, but there is a tendency that depth of field (depth of observation) is shallower.

For example, FIGS. 15(A) and 15(B) show conceptual diagrams of an image pickup unit of a conventional endoscope apparatus. Between the diagrams, FIG. 15(A) is a conceptual diagram showing a state in which a subject at a near point is focused (a focused state). Further, FIG. 15(B) is a conceptual diagram showing a state in which a subject at a far point is focused (a focused state).

As shown in FIGS. 15(A) and 15(B), an image pickup unit 109 is mainly configured with an image pickup objective lens 133 which forms optical images of subjects 101(e and k) and an image pickup device 131 which receives an optical image formed by the image pickup objective lens 133 and performs photoelectric conversion to generate an image signal. An optical axis O of the image pickup objective lens 133 is set so as to almost correspond to a center of a light receiving plane 131b of the image pickup device 131. A color filter which optically performs color separation is arranged on a front of a light receiving portion 131a of the image pickup device 131.

It is assumed that, in the image pickup unit 109 in such a configuration, as shown in, for example, FIG. 15(A) a setting is made so that an optical image of the subject 101k existing at a near point (a short-distance position) is formed on the light receiving plane 131b of the image pickup device 131 in a focused state. A distance, that is, an optical path length from the image pickup objective lens 133 to the light receiving plane 131b (a plane denoted by reference symbol k in FIG. 15(A)) of the image pickup device 131 at this time, is denoted by reference symbol OPL1. In this setting state, an optical image of the subject 101e existing at a far point (a long-distance position) exists at a position denoted by reference symbol k.

On the other hand, in order to cause the optical image of the subject 101e existing at the far point (the long-distance position) to be in a focused state on the light receiving plane 131b of the image pickup device 131, it is necessary to move the light receiving plane 131b of the image pickup device 131 from the state shown in FIG. 15(A) to a position near to the image pickup objective lens 133 in a direction along the optical axis O, that is, a position corresponding to a plane denoted by reference symbol e as shown in FIG. 15(B). A distance from the image pickup objective lens 133 to the light receiving plane 131b (a plane denoted by reference symbol k in FIG. 15(B)) of the image pickup device 131 is an optical path length OPL2. That is, the near-point optical path length OPL1>the far-point optical path length OPL2 is satisfied.

Therefore, for the conventional endoscope apparatus, various devices for configuring the endoscope apparatus such that an image can be acquired in which a focused state is obtained at a near point and a far point without providing the focus adjustment mechanism are proposed, for example, by Japanese Patent Application Laid-Open Publication No. 11-197097.

An endoscope apparatus disclosed by Japanese Patent Application Laid-Open Publication No. 11-197097 and the like is such that an optical path of a light flux which has passed through an objective lens is separated by a prism so that the separated light fluxes are caused to enter an image pickup device for a far point and an image pickup device for a near point set to different optical path lengths, and an image signal outputted from each of the image pickup device is acquired. Due to the configuration, in the endoscope apparatus disclosed by Japanese Patent Application Laid-Open Publication No. 11-197097, a plurality of images focused at different distances can be simultaneously picked up and displayed.

SUMMARY OF THE INVENTION

An endoscope apparatus of one aspect of the present invention includes: an image pickup unit comprising a plurality of image pickup devices and an optical path dividing member for dividing a light beam entering from an objective lens into a plurality of optical paths and leading the optical paths to the respective plurality of image pickup devices, wherein optical path lengths of the plurality of optical paths are different from one another; a contrast comparing member for comparing contrasts of a plurality of images based on a plurality of image signals outputted from the plurality of image pickup devices, respectively; an image selecting member for selecting and outputting only an image signal from one image pickup device among the plurality of image pickup devices, on a basis of a result of the comparison by the contrast comparing member; and a driving member for moving a movable lens so that a difference among the contrasts of the plurality of images based on the plurality of image signals outputted from the plurality of image pickup devices, respectively, is largest, wherein a part of the objective lens is configured to be movable in an optical axis direction as the movable lens.

BRIEF DESCRIPTION OF THE DRAWINGS

FIGS. 15(A) and 15(B) show a concept of an image pickup unit of a conventional endoscope apparatus, and FIG. 15(A) and FIG. 15(B) are a conceptual diagram showing a state in which a subject existing at a near point is focused (a focused state) and a state in which a subject existing at a far point is focused (a focused state), respectively.

DETAILED DESCRIPTION OF THE PREFERRED EMBODIMENTS

Figure 1:
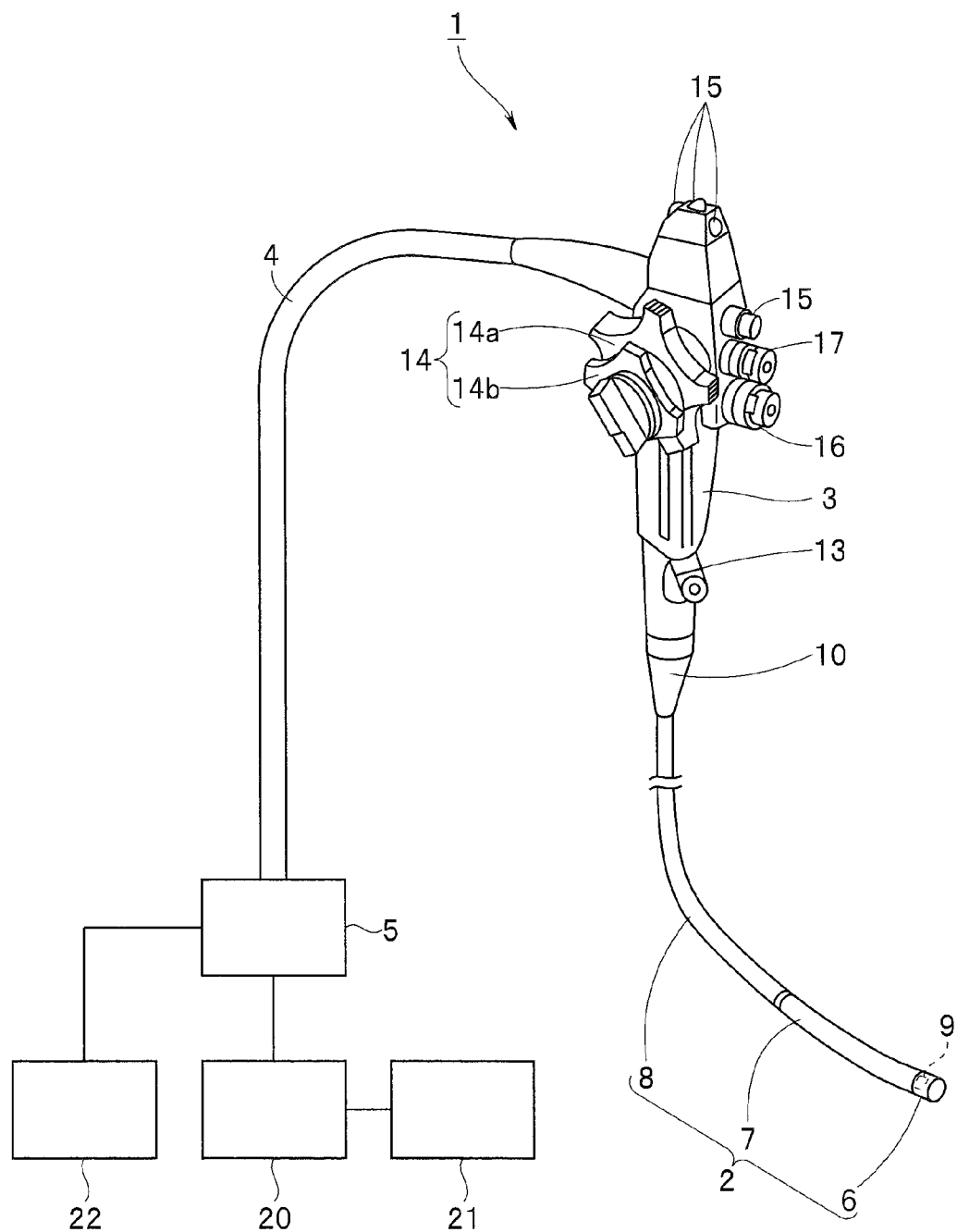
FIG. 1 is a diagram showing a schematic configuration of an endoscope apparatus of a first embodiment of the present invention.

The present invention will be described below by embodiments shown in drawings.

Note that, in each drawing used in the following description, each component may be shown with a different scale so that each component may be of a size enough to be recognized on the drawing. Therefore, the present invention is not limited to the number of components, shapes of the components, ratio of sizes of the components and relative positional relationships among the respective components of the embodiments shown on the drawings.

First Embodiment

First, a schematic configuration of an endoscope apparatus of a first embodiment of the present invention will be described. FIG. 1 is a diagram showing the schematic configuration of the endoscope apparatus of the first embodiment of the present invention.

As shown in FIG. 1, the endoscope apparatus of the present embodiment is mainly configured with an endoscope 1, a processor unit 20, a display device 21 which is an output device, a light source device 22 and the like.

The endoscope 1 is mainly configured with an insertion portion 2, an operation portion 3, a universal cable 4 and the like.

The insertion portion 2 is a long member in an elongated shape to be inserted into an examinee's body cavity to be an observation target. The insertion portion 2 is configured by connecting a distal end portion 6, a bending portion 7 and a flexible tube portion 8 in that order from a distal end side. Inside the distal end portion 6, an illumination optical system (not shown) which emits and diffuses an illuminating light from a light guide (not shown) or the like, from a front, and an image pickup unit 9 provided with an image pickup optical system (an objective lens 33A), a plurality of image pickup devices 31 and 32 (see FIG. 2 and the like to be described later) and the like are included. The bending portion 7 is configured so that it bends, for example, in four directions, up and down, left and right. The flexible tube portion 8 is constituted by a long, flexible tube-shape member. The operation portion 3 is connected to a proximal end portion of the insertion portion 2.

The proximal end portion of the insertion portion 2 is coupled with and fixed to a distal end side of the operation portion 3 via a bend preventing member 10. At a part near a distal end of the operation portion 3, a treatment instrument insertion opening 13 for causing, for example, a treatment instrument or the like to be inserted into the insertion portion 2 is provided.

A bending operation portion 14, an air/water feeding button 16, a suction button 17, and a plurality of operation members 15 including operation buttons and the like for performing other various operations, and the like are arranged on an outer surface of the operation portion 3.

Among these, bending operation knobs 14a and 14b for performing a bending operation of, for example, the bending portion 7 of the insertion portion 2 are arranged on the bending operation portion 14. Such a configuration is made that, by a user appropriately performing a rotation operation of each of the bending operation knobs 14a and 14b, a bending wire (not shown) inserted through the insertion portion 2 from the operation portion 3, connected to the bending portion 7 is pulled and loosened. The bending portion 7 is bent in vertical and horizontal directions in response to the operation. For example, in addition to a release switch, a freeze switch and the like, an observation mode switching switch for performing a switching operation between normal observation and special observation, and the like are included in the plurality of operation members 15. The universal cable 4 extends from a lateral side of the operation portion 3.

The light guide, various signal lines, a power supply line and the like (not shown) are insertedly arranged inside the universal cable 4. These light guide, various signal lines, power supply line and the like (not shown) are inserted through insides of the universal cable 4, the operation portion 3 and the insertion portion 2, and their end portions reach the distal end portion 6 of the insertion portion 2. At a distal end portion of the universal cable 4, an endoscope connector 5 is arranged.

The endoscope connector 5 can be freely attached to or detached from the processor unit 20, which is an external device, and is configured so that electrical connection is secured between the endoscope connector 5 and the processor unit 20 when the endoscope connector 5 is connected to the processor unit 20. Further, the endoscope connector 5 is adapted such that a cable (not shown; an optical fiber cable and the like are inserted therein) extending from the light source device 22 is connected. Configuration is such that, when the cable is connected to the endoscope connector 5, a light emitted from the light source device 22 reaches the distal end portion 6 through the light guide (not shown) inserted through the universal cable 4, the operation portion 3 and the insertion portion 2 via the cable and the endoscope connector 5 to emit an illuminating light from a distal end face in a forward direction.

The processor unit 20 is a control unit provided with a control circuit which performs various image signal processing in response to an output signal from the image pickup unit 9 of the endoscope 1 and performs general control of the endoscope 1. As described above, the processor unit 20 is connected to the universal cable 4 via the endoscope connector 5.

The display device 21, which is an output device, is electrically connected to the processor unit 20, and it is a configuration unit provided with a display panel which displays an image in response to an image signal for display outputted from the processor unit 20, and the like.

The light source device 22 is connected to the universal cable 4 via the cable (not shown) and the endoscope connector 5, and it is a configuration unit to be a light source of an illuminating light to be emitted from a distal end front of the insertion portion 2 via the light guide inserted through the insides of the universal cable 4, the operation portion 3 and the insertion portion 2.

In the endoscope apparatus of the present embodiment, various components exist in addition to the configuration members, configuration units and the like described above. However, since the other components are not directly related to the present invention, description and illustration thereof are omitted on an assumption that components similar to those used in a conventional general endoscope apparatus are applied as the components.

Figure 2:
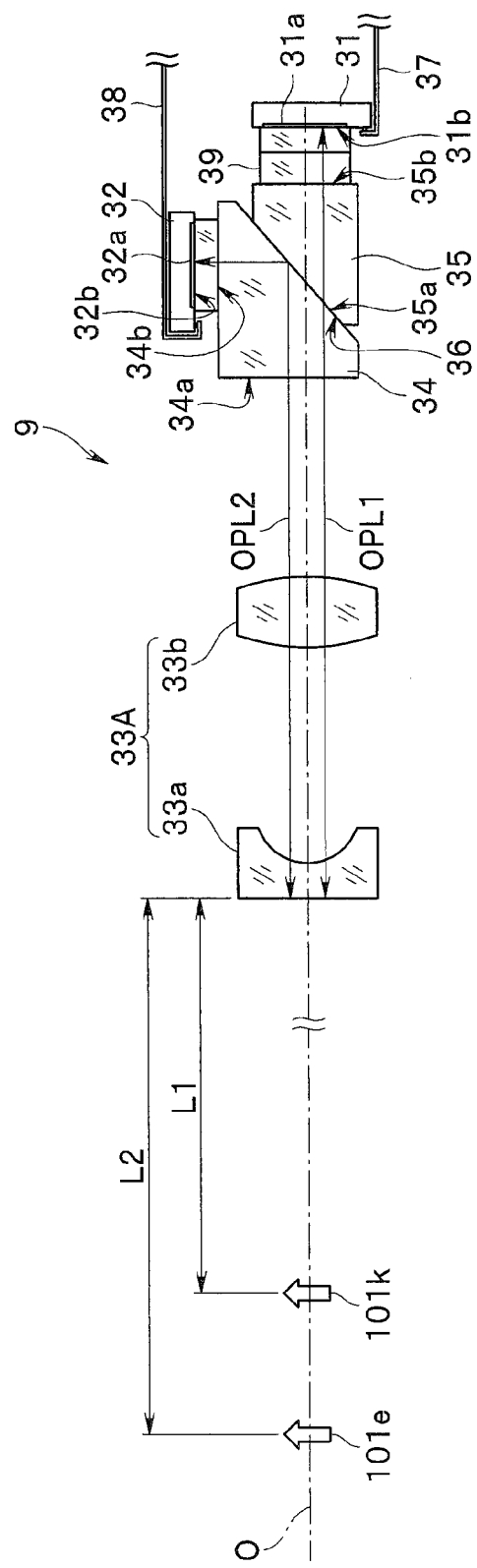
FIG. 2 is a diagram showing a schematic configuration of an image pickup unit arranged in a distal end portion of an insertion portion of an endoscope in the endoscope apparatus of FIG. 1.

Description will be made below on a configuration of the image pickup unit 9 arranged in the distal end portion 6 of the insertion portion 2 of the endoscope 1 in the endoscope apparatus of the present embodiment configured as described above. FIG. 2 is a diagram showing a schematic configuration of the image pickup unit arranged in the distal end portion of the insertion portion of the endoscope in the endoscope apparatus of the present embodiment. Note that FIG. 2 also shows a state at the time of causing the image pickup unit to face subjects (101*e* and 101*k*) to be observation targets.

The image pickup unit 9 applied to the endoscope apparatus of the present embodiment is mainly configured with the objective lens 33A, two prisms (34 and 35), two image pickup devices (31 and 32), a high-refractive optical device 39 and the like as shown in FIG. 2.

The objective lens 33A is configured with a plurality of optical lenses (a first lens 33*a* and a second lens 33*b*), lens barrel members (not shown) holding the plurality of optical lenses, and the like, and it is a configuration unit forming an image pickup optical system of the image pickup unit 9. Note that the first lens 33*a* of the objective lens 33A is arranged facing an observation window (not shown) formed on a distal end face of the distal end portion 6 of the insertion portion 2 of the endoscope 1. Due to the configuration, a light flux from a subject enters the objective lens 33A.

On an optical axis O of the objective lens 33A and behind the objective lens 33A, the first prism 34 is arranged which is optical path dividing means for causing a light flux from a subject transmitted through the objective lens 33A to come in and dividing the incident light in a direction orthogonal to the optical axis O and a direction along the optical axis O and which is a first half prism. Therefore, the first prism 34 is formed having a plane of incidence 34*a*, a half mirror plane 36 and a plane of emission 34*b*.

The plane of incidence 34*a* of the first prism 34 is a plane which a light flux from a subject enters, and it is formed facing the objective lens 33A and formed by a plane parallel to a plane orthogonal to the optical axis O.

The half mirror plane 36 of the first prism 34 is formed having an inclination angle of about 45 degrees relative to the plane of incidence 34*a*, and reflectance of the half mirror plane 36 is set such that 50% or more of a quantity of light of the light flux from the subject is reflected in the direction orthogonal to the optical axis O while a remaining quantity of light is transmitted in the direction along the optical axis O.

That is, the half mirror plane 36 plays a role of dividing a light flux from a subject and leading a part of the light flux (50% or more of a quantity of light) to a light receiving plane 32*b* of the second image pickup device 32 to be described later while leading a remaining part of the light flux to a light receiving plane 31*b* of the first image pickup device 31 to be described later.

The plane of emission 34*b* of the first prism 34 is a plane from which a reflected light bent by an angle of about 90 degrees by the half mirror plane 36 is emitted and is formed by a plane parallel to the optical axis O.

The second image pickup device 32 is arranged on an optical path of the reflected light bent by the angle of about 90 degrees by the half mirror plane 36. The light receiving plane 32*b* of the second image pickup device 32 is arranged such that it faces the plane of emission 34*b*. That is, the second image pickup device 32 is arranged at a position of receiving a part of a light flux emitted from the first prism 34 (a light reflected from the half mirror plane 36).

On the other hand, the second prism 35 is arranged on an optical path of a transmitted light which is transmitted through the half mirror plane 36 and emitted backward along the optical axis O. The second prism 35 plays a role of leading a light flux transmitted through the half mirror plane 36 backward along the optical axis O. Therefore, the second prism 35 is formed having a plane of incidence 35*a* which is in contact with the half mirror plane 36 of the first prism 34 and a plane of emission 35*b* parallel to the plane orthogonal to the optical axis O. The first image pickup device 31 is arranged behind the second prism 35 on an optical path of a light flux transmitted through the half mirror plane 36. The light receiving plane 31b of the first image pickup device 31 is arranged such that it faces the plane of emission 35b. Therefore, the first image pickup device 31 is arranged at a position of receiving a light flux emitted from the second prism 35.

The high-refractive optical device 39 is arranged being sandwiched between the plane of emission 35b of the second prism 35 and the first image pickup device 31. The high-refractive optical device 39 is an optical member arranged in order to shorten an optical path length and is an optical member with a high refractive index. By arranging the high-refractive optical device 39, it is possible to set a linear dimension of a rigid part at the distal end portion 6 of the insertion portion 2 of the endoscope 1 short, which contributes to downsizing of the distal end portion 6.

Flexible printed circuits (FPCs) 37 and 38 are electrically connected to the image pickup devices 31 and 32, respectively. Such a configuration is made that image signals generated by the respective image pickup devices 31 and 32 are transmitted from the FPCs 37 and 38 to the processor unit 20 in the end via a signal cable (not shown) inserted through the insertion portion 2, the operation portion 3 and the universal cable 4.

Note that, as the first and second image pickup devices 31 and 32, a photoelectric conversion device which is a solid-state image pickup device, such as a CCD image sensor using a circuit device such as a CCD (charge coupled device) or a MOS-type image sensor using a CMOS (complementary metal oxide semiconductor) or the like may be applied. Each of the two image pickup devices 31 and 32 is provided with a color filter on its light receiving plane and is configured to be capable of outputting a signal of a color image.

Here, a distance (an optical path length OPL1) from a front of the first lens 33a of the objective lens 33A to the light receiving plane 31b of the first image pickup device 31 and a distance (an optical path length OPL2) from the front of the first lens 33a of the objective lens 33A to the light receiving plane 32b of the second image pickup device 32 are set so that OPL1>OPL2 is satisfied. That is, optical path lengths of a plurality of light beams to be led to the plurality of image pickup devices are set to be mutually different.

Therefore, the first image pickup device 31 arranged on a side for which a setting is made so that a relatively long optical path length (the first optical path length OPL1) is obtained is an image pickup device for a near point capable of obtaining an image for the near point, that is, an image in which the subject 101k existing at the near point is focused. Further, the second image pickup device 32 arranged on a side for which a setting is made so that a relatively short optical path length (the second optical path length OPL2) is obtained is an image pickup device for a far point capable of obtaining an image for the far point, that is, an image in which the subject 101e existing at the far point is focused.

In other words, the different two optical path lengths (OLP1 and OLP2) (OPL1 and OPL2) are set so that images of objects positioned at mutually different object distances (a far point and a near point), respectively, are formed on the plurality of image pickup devices 31 and 32, respectively.

Note that, it is assumed in the description of the present embodiment that, when the word "near point" is used, it is, for example, a case where a distance from the front of the first lens 33a of the objective lens 33A (referred to as a first object distance) is shorter than 20 mm. In the example shown in FIG. 2, it is assumed that the following is satisfied: a distance L1 to the subject 101k near the objective lens 33A (existing at a position at a short distance)=shorter than 20 mm. On the other hand, it is similarly assumed in the description of the present embodiment that, when the word "far point" is used, it is, for example, a case where a distance from the front of the first lens 33a of the objective lens 33A (referred to as a second object distance) is 20 mm or longer. In the example shown in FIG. 2, it is assumed that the following is satisfied: a distance L2 to the subject 101e existing at a position at a longer distance than the objective lens 33A=20 mm or longer.

In the image pickup unit 9 in the endoscope apparatus of the present embodiment configured as described above, a light flux which enters the objective lens 33A from a subject side and transmitted straight is divided in two directions by the half minor plane 36 of the first prism 34. One of the divided light fluxes is bent by an angle of 90 degrees on the half mirror plane 36, and an image is formed on the light receiving plane 32b of the first image pickup device 32. At this time, the image formed on the light receiving plane 32b of the second image pickup device 32 is an image in which the subject 101e at the far point is focused, and the subject 101k at the near point is in a state of being out of focus (being blurred). The other divided light flux is transmitted straight through the half mirror plane 36, and an image is formed on the light receiving plane 31b of the first image pickup device 31. At this time, the image formed on the light receiving plane 31b of the first image pickup device 31 is an image in which the subject 101k at the near point is focused, and the subject 101e at the far point is in a state of being out of focus (being blurred).

In a usual case, there is a tendency that luminance in an image of a subject at a far point becomes lower in comparison with a subject at a near point. In consideration thereof, in the image pickup unit 9 in the present embodiment, the half minor plane 36 is set so that 50% or more of a quantity of light of a light flux from a subject is led to a side of the second image pickup device 32 for a far point as described above. That is, due to the configuration, a quantity of light led to the side of the second image pickup device 32 for a far point is set to be larger than a quantity of light led to a side of the first image pickup device 31 for a near point. Therefore, it is desirable to, by adjusting the setting of the half mirror plane 36, make a setting so that an image for a near point on the basis of an image signal acquired by the first image pickup device 31 for a near point and an image for a far point on the basis of an image signal acquired by the second image pickup device 32 for a far point become images with almost equal brightness.

In this way, two kinds of image signals from the respective image pickup devices 31 and 32 are outputted from the image pickup unit 9. These output signals (image signals) are transmitted to the processor unit 20 as described above. In response to input of the image signals, the processor unit 20 executes necessary image processing.

Figure 3:
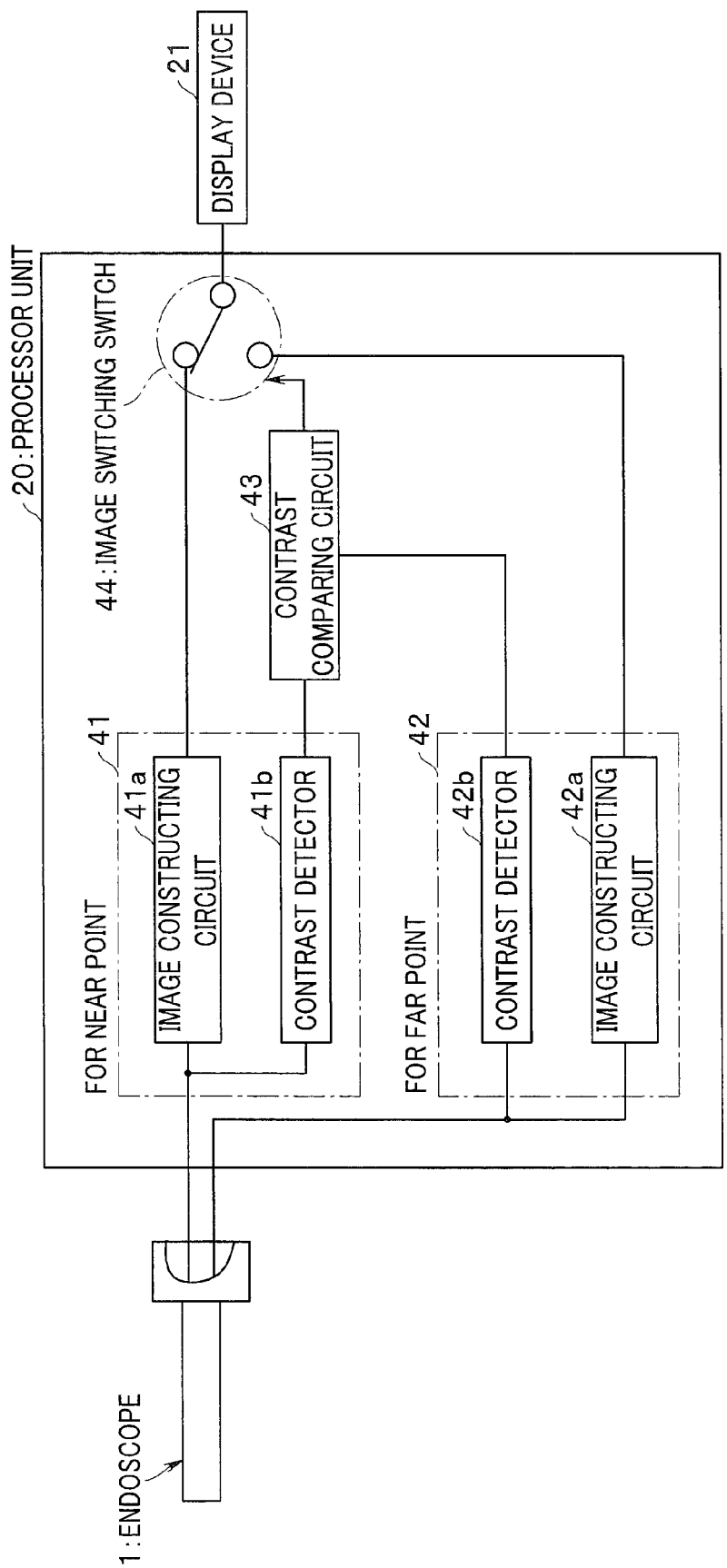
FIG. 3 is a block configuration diagram showing only (image-processing-circuit-related) components related to the present invention in an internal configuration of a processor unit in the endoscope apparatus of FIG. 1.

Here, an image-processing-circuit-related configuration in an internal configuration of the processor unit 20 will be described briefly. FIG. 3 is a block configuration diagram showing only (image-processing-circuit-related) components related to the present invention in the internal configuration of the processor unit in the endoscope apparatus of the present embodiment.

As shown in FIG. 3, the processor unit 20 in the endoscope apparatus of the present embodiment is provided with an image processing circuit 41 for a near point, an image processing circuit 42 for a far point, a contrast comparing circuit 43, an image switching switch 44 and the like.

The image processing circuits 41 and 42 are configured having image constructing circuits 41a and 42a, contrast detectors 41*b* and 42*b* and the like. The image constructing circuits 41*a* and 42*a* are circuit units which, in response to an image signal outputted from the image pickup unit 9 of the endoscope 1, constructs an image and perform signal processing for generating, for example, an image signal for display in a form appropriate for display. The contrast detectors 41*b* and 42*b* are circuit units which, in response to an image signal outputted from the image pickup unit 9 of the endoscope 1, detects a high-contrast part in an image.

The contrast comparing circuit 43 is a circuit unit which, in response to an output from the contrast detector 41*b* for a near point and an output from the contrast detector 42*b* for a far point, compares both outputs. That is, the contrast comparing circuit 43 is contrast comparing means for comparing contrasts of a plurality of images based on a plurality of image signals outputted from the plurality of image pickup devices (31 and 32).

The image switching switch 44 is a switching member for selectively outputting one of outputs from the two image pickup devices 31 and 32 to an output device (the display device 21). For the purpose, the image switching switch 44 intervenes between the image constructing circuits 41*a* and 42*a* and the display device 21 which is an output device. The image switching switch 44 is controlled by the processor unit 20. That is, the processor unit 20 performs switching control of the image switching switch 44 in response to an output signal of a contrast comparison result from the contrast comparing circuit 43 (the contrast comparing means) and selectively outputs only an image signal from one of the plurality of image pickup devices (31 and 32) (for example, an image signal of an image with a highest contrast) to the display device 21. In this case, the processor unit 20 functions as image selecting means.

Therefore, due to such a configuration, the processor unit 20 is configured so as to, when receiving an output from the image pickup unit 9, construct an image signal for display and, at the same time, perform switching control of the image switching switch 44 on the basis of an output of the contrast comparing circuit 43 (a contrast comparison result), and selectively output either an output signal from the image constructing circuit 41*a* for a near point (an image signal for a near point) or an output signal from the image constructing circuits 42*a* for a far point (an image signal for a far point) to the display device 21.

Here, there is a tendency that a contrast of an image in which a subject is focused is high while a contrast is low in a state of being out of focus (being blurred). Therefore, the processor unit 20 always compares contrast of respective image signals of the first image pickup device 31 and the second image pickup device 32, selects an image signal with a higher contrast, outputs the image signal to the display device 21 and performs control to cause the display device 21 to display the image signal on its display screen.

As described above, according to the first embodiment, the image pickup unit 9 is provided with the first prism 34 provided with the half mirror plane 36 which divides a light flux which enters the objective lens 33A from a subject side and is transmitted straight in two directions and the two image pickup devices 31 and 32 which receive the two respective light fluxes divided by the half mirror plane 36 and is configured to be able to, by appropriately setting an optical path length of each of the two light fluxes divided by the half mirror plane 36, acquire two image signals, that is, an image signal indicating an image in which a far point (a distance to the subject: 20 mm or longer) is focused and an image signal indicating an image in which a near point (a distance to the subject: shorter than 20 mm) is focused. The processor unit 20 is configured so as to, for the two image signals acquired by the image pickup unit 9, automatically compare contrasts thereof, output an image with a high contrast and cause the display device 21 to display the image.

Thereby, it is always possible to cause an image in a state of being focused to be displayed by the display device 21. Further, it is possible to acquire an image signal for a near point and an image signal for a far point without moving the image pickup optical system, the image pickup devices and the like in an optical axis direction. That is, it is possible to eliminate necessity of a complicated configuration including a driving source such as an actuator and the like, a movable mechanism and the like and enable a simpler configuration, it is possible not only to contribute to improvement of durability and reliability of the apparatus but also to realize downsizing of the apparatus.

Furthermore, in the image pickup unit 9 in the present embodiment, the reflectance of the half mirror plane 36 is set so that 50% or more of a quantity of light of a light flux from a subject is led to the side of the second image pickup device 32 for a far point. Due to the configuration, it is possible to make a setting so that an image for a near point on the basis of an image signal acquired by the first image pickup device 31 for a near point and an image for a far point on the basis of an image signal acquired by the second image pickup device 32 for a far point become images with almost equal brightnesses. Therefore, it is possible to conduct observation by a display image with a favorable brightness irrespective of a distance to a subject.

Since such a configuration is made that a light flux from a subject is radiated to the first image pickup device 31 for a near point via the two prisms 34 and 35, there is a tendency that a rigid length of the distal end portion 6 of the insertion portion 2 of the endoscope 1 becomes long. Therefore, in the present embodiment, it is devised to shorten an optical path length by arranging the high-refractive optical device 39 between the plane of emission 35*b* of the second prism 35 and the first image pickup device 31. Thus, since the high-refractive optical device 39 is provided, it is possible to prevent the rigid length from being long and, therefore, contribute to downsizing of the distal end portion 6.

At the time of arranging the plurality of image pickup devices (two in this example) inside the distal end portion 6, it is possible to arrange the two image pickup devices at positions away from each other by providing one on an optical path corresponding to the optical axis O of the image pickup optical system and providing the other on an optical path orthogonal to the optical axis O of the image pickup optical system. Therefore, in comparison with a configuration in which a plurality of (two) image pickup devices are arranged, for example, side by side, it is possible to prevent the distal end portion 6 from being upsized in a diameter direction. Further, it is possible to efficiently distribute arrangements of the flexible printed circuits which are extended from the two image pickup devices, respectively, and on which a lot of various electric members are implemented and arranged, and, therefore, prevent the apparatus from being upsized.

In the first embodiment described above, an example is shown in which, in response to output of two image signals from the two image pickup devices 31 and 32 of the image pickup unit 9, the processor unit 20 automatically compares contrasts, and performs control to select an image signal with a higher contrast and output the image signal to the display device 21.

In addition to the configuration example of automatically selecting an appropriate image and causing the image to be displayed as described above, a configuration as shown below may be also adopted. That is, in response to output of two image signals from the two image pickup device 31 and 32 of the image pickup unit 9, the processor unit 20 causes two images to be displayed on the display screen of the output device (the display device 21). Such a configuration is made that the user can arbitrarily perform display switching, for example, among displaying one of the two images being displayed, on the full screen of the display device 21, displaying the other similarly, and the like. That is, a configuration is also possible in which, at the time of causing two images based on two image signals acquired by the two image pickup device 31 and 32 of the image pickup unit 9 to be displayed, switching can be performed with the user's intension among display forms, such as a form of causing the two images to be simultaneously displayed, a form of causing only one image to be displayed, and a form of causing only the other image to be displayed.

Further, though a configuration example is shown in which the image pickup unit 9 is provided with the two image pickup device 31 and 32 in the first embodiment described above, such a configuration example is not limiting. For example, a configuration example is also conceivable in which the number of image pickup devices to be arranged is three or more. In this case, it is possible to easily cope with the configuration, for example, by further adding half prisms, which are optical path dividing means for dividing a light flux which enters the image pickup unit 9.

Second Embodiment

Next, a second embodiment of the present invention will be described. A configuration of the present embodiment is basically almost similar to that of the first embodiment described above but is slightly different only in a configuration of an objective lens constituting an image pickup optical system of an image pickup unit. Therefore, components similar to those of the first embodiment described above are given same reference symbols, and detailed description thereof will be omitted. Only different parts will be described below.

Figure 4:
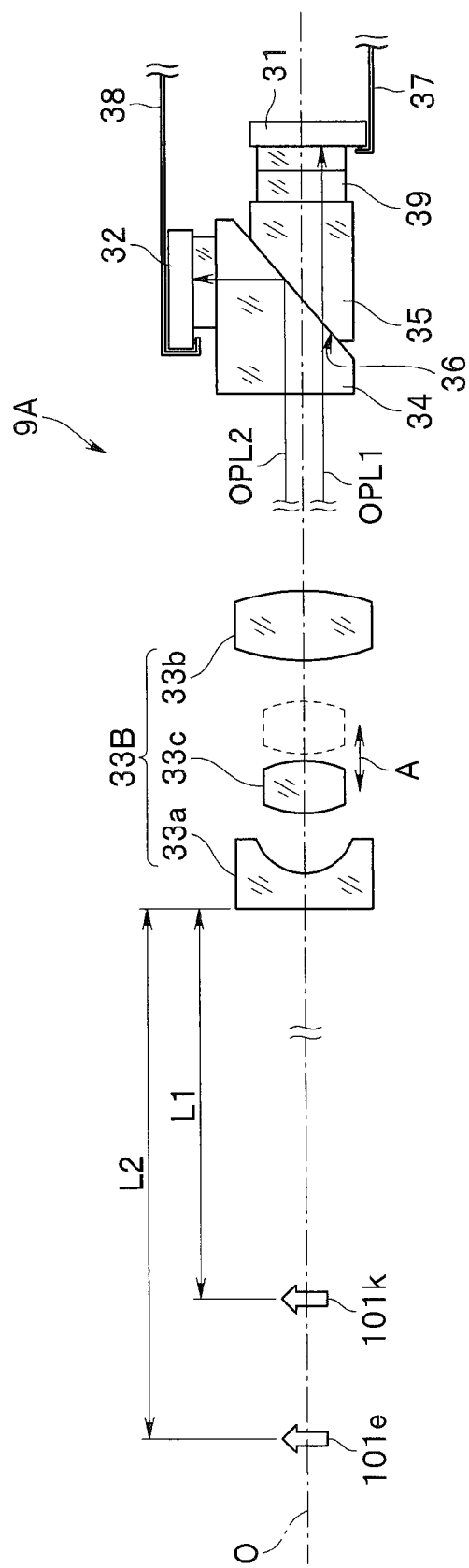
FIG. 4 is a diagram showing an outline of an image pickup unit in an image pickup unit in an endoscope apparatus of a second embodiment of the present invention.

FIG. 4 is a diagram showing an outline of the image pickup unit in an endoscope apparatus of the second embodiment of the present invention. As shown in FIG. 4, in an image pickup unit 9A in the endoscope apparatus of the present embodiment, a so-called zoom-type objective lens capable of performing a magnification changing operation is applied as an objective lens 33B, which is an image pickup optical system. The objective lens 33B is configured with a first lens 33a and a second lens 33b fixedly arranged in the image pickup unit 9A, a plurality of optical lens groups, such as a zoom lens system 33c arranged to freely move forward and backward in an optical axis O direction (a direction of an arrow A shown in FIG. 4) relative to the first lens 33a and the second lens 33b, a driving mechanism and a driving source (neither of them is shown) for appropriately causing the zoom lens system 33c to move forward or backward in the optical axis O direction on the basis of a predetermined operation instruction (a manual operation instruction or an automatic operation instruction), and the like. Other components are similar to those of the first embodiment described above.

As described above, according to the second embodiment, advantages quite similar to those of the first embodiment described above can be also obtained in the endoscope apparatus adopting the image pickup unit 9A to which the objective lens 33B, which is a zoom-lens-type photographing optical system, is applied.

Third Embodiment

Figure 5:
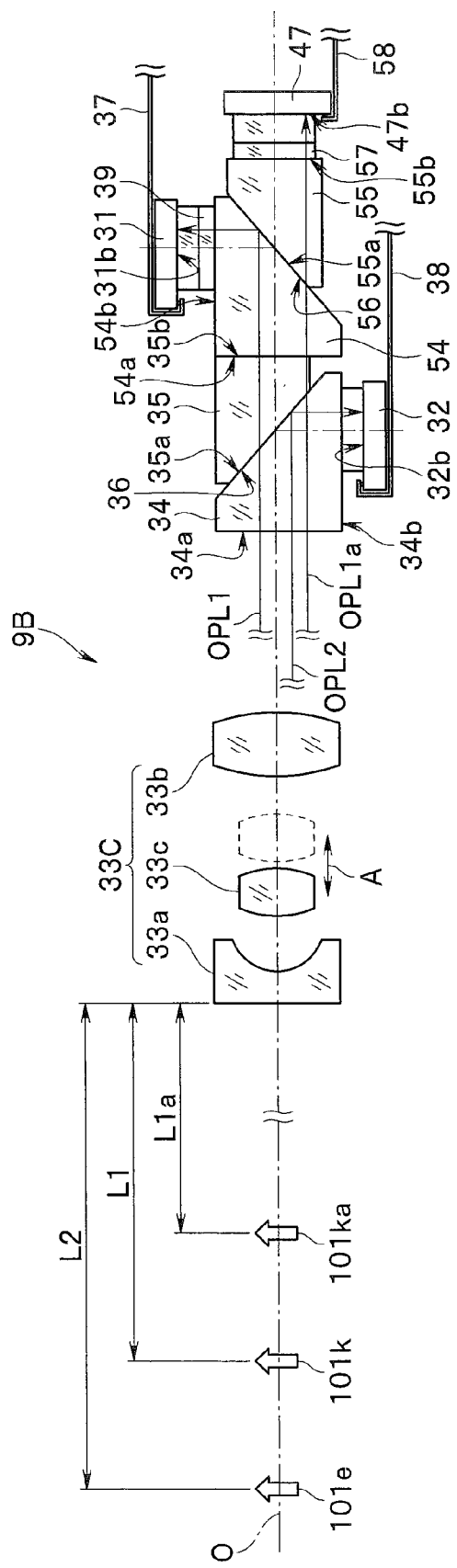
FIG. 5 is a diagram showing an outline of an image pickup unit in an endoscope apparatus of a third embodiment of the present invention.

Next, a third embodiment will be described. A configuration of the present embodiment is basically almost similar to that of the second embodiment described above. In the configuration of the present embodiment, three images corresponding to distances to subjects can be simultaneously acquired by providing three image pickup devices for an image pickup unit as shown in FIG. 5. In this case, the present embodiment is different from the first embodiment described above in a point that the configuration is made so that the three images can correspond to an image signal indicating an image in which a far point (the distance to the subject: 20 mm or longer) is focused and an image signal indicating an image in which a near point (the distance to the subject: 1 mm or longer and shorter than 20 mm) is focused, similarly to the first and second embodiments described above, and, furthermore, an image signal indicating an image in which a nearest neighbor at a position nearer than the above near point (the distance to the subject: about 0.5 mm or longer and shorter than 1 mm) is focused. In description below, components similar to those of the first and second embodiments described above are given same reference symbols, and detailed description thereof will be omitted. Only different parts will be described.

In general, in a case of applying a zoom lens as an image pickup optical system, there is a tendency that depth of field becomes shallow when a long focal distance within a zoom range of the zoom lens is set. Therefore, in the endoscope apparatus of the present embodiment, it is attempted to, by acquiring three images corresponding to distances to subjects using the three image pickup devices, obtain a wider depth of field.

FIG. 5 is a diagram showing an outline of the image pickup unit in the endoscope apparatus of the third embodiment of the present invention. An image pickup unit 9B in the endoscope apparatus of the present embodiment is similar to the second embodiment described above in that a zoom-type objective lens capable of performing a magnification changing operation is applied as an objective lens 33C, which is an image pickup optical system, as shown in FIG. 5.

On the other hand, in the present embodiment, four prisms are arranged on an optical axis O of the objective lens 33C and behind the objective lens 33C as shown in FIG. 5. That is, a first prism 34, a second prism 35, a third prism 54 and a fourth prism 55 are arranged behind the objective lens 33C in that order from a front side.

The first prism 34 is optical path dividing means formed having a plane of incidence 34a, a first half mirror plane 36 and a plane of emission 34b, and it is a first half prism. Due to the configuration, the first prism 34 causes a light flux from a subject transmitted through the objective lens 33C to enter the plane of incidence 34a and divides a part of the incident light in a direction orthogonal to the optical axis O (a direction leading the light to a light receiving plane 32b of a second image pickup device 32) and a direction along the optical axis O (backward) on the half mirror plane 36. The first prism 34 is configured similarly to the first prism 34 of the first embodiment described above and provided with the same function. Here, the second image pickup device 32 is an image pickup device which generates an image signal for a far point.

The second prism 35 is formed having a plane of incidence 35a which is in contact with the first half mirror plane 36 of the first prism 34 and a plane of emission 35b parallel to a plane orthogonal to the optical axis O. Due to the configuration, the second prism 35 leads a light flux transmitted through the first half mirror plane 36 backward along the optical axis O. The second prism 35 is also configured similarly to the second prism 35 of the first embodiment described above and provided with an almost similar function.

The third prism 54 exists behind the second prism 35 and arranged on an optical path of a light flux transmitted through the second prism 35 after being transmitted through the half mirror plane 36 of the first prism 34. The third prism 54 is optical path dividing means formed having a plane of incidence 54a, a second half mirror plane 56 and a plane of emission 54b, and it is a second half prism. The plane of incidence 54a of the third prism is formed such that it is parallel to the plane orthogonal to the optical axis O so as to be in contact with the plane of emission 35b of the second prism 35. The second half mirror plane 56 divides a part of an incident light in the direction orthogonal to the optical axis O (a direction leading the light to a light receiving plane 31b of a first image pickup device 31) and the direction along the optical axis O (backward). Therefore, the second half mirror plane 56 of the third prism 54 is formed having an inclination angle of about 45 degrees relative to the plane of incidence 54a. In this case, an inclination direction of the second half mirror plane 56 is set such that an inclination in a direction opposite to the half mirror plane 36 is provided. That is, the inclination of the second half mirror plane 56 is set so as to have an angle of about 90 degrees relative to the inclination of the half mirror plane 36. Due to the configuration, the second half mirror plane 56 is formed so as to reflect a partial light flux of an incident light from the plane of incidence 54a in a direction toward the direction orthogonal to the optical axis O and opposite to a direction of bending of the light flux by the first half mirror plane 36 (the light receiving plane 31b of the first image pickup device 31 to be described later) while transmitting a remaining light flux to the direction along the optical axis O (backward). That is, the second half mirror plane 56 plays a role of dividing an incident light flux and leading a part of the light flux to the light receiving plane 32b of the first image pickup device 31 to be described later while leading the other remaining part of the light flux backward along the optical axis O to a light receiving plane 47b of a third image pickup device 47 to be described later.

Further, the plane of emission 54b of the third prism 54 is a plane from which a reflected light bent by an angle of about 90 degrees by the second half mirror plane 56 is emitted and is formed by a plane parallel to the optical axis O. The first image pickup device 31 is arranged on an optical path of the reflected light bent by the angle of about 90 degrees by the second half mirror plane 56. The light receiving plane 31b of the first image pickup device 31 is arranged such that it faces the plane of emission 54b. That is, the first image pickup device 31 is arranged at a position of receiving a part of a light flux emitted from the third prism 54 (a light reflected from the second half mirror plane 56). Here, the first image pickup device 31 is an image pickup device which generates an image signal for a near point.

The fourth prism 55 is formed having a plane of incidence 55a which is in contact with the second half mirror plane 56 of the third prism 54 and a plane of emission 55b parallel to the plane orthogonal to the optical axis O. Due to the configuration, the fourth prism 55 leads a light flux transmitted through the second half mirror plane 56 backward along the optical axis O. The third image pickup device 47 is arranged on an optical path of the light flux transmitted through the fourth prism 55 after being transmitted through the second half mirror plane 56, behind the fourth prism 55. The light receiving plane 47b of the third image pickup device 47 is arranged facing the plane of emission 55b of the fourth prism 55. Therefore, the third image pickup device 47 is arranged at a position of receiving a light flux emitted from the fourth prism 55. Here, the third image pickup device 47 is an image pickup device which generates an image signal for a nearest neighbor. A photoelectric conversion device, which is a solid-state image pickup device such as a CCD image sensor or a MOS-type image sensor, is also applied to the third image pickup device 47 similarly to the first image pickup device 31 and the second image pickup device 32.

A high-refractive optical device 57 is arranged being sandwiched between the plane of emission 55b of the fourth prism 55 and the third image pickup device 47. The high-refractive optical device 57 is an optical member arranged in order to shorten an optical path length similarly to the high-refractive optical device 39 of the first embodiment described above.

Flexible printed circuits (FPCs) 37, 38 and 58 are electrically connected to the image pickup devices 31, 32 and 47, respectively. Image signals generated by the image pickup devices 31, 32 and 47 are transmitted from the FPCs 37, 38 and 58 to the processor unit 20 in the end via a signal cable (not shown) inserted through an insertion portion 2, an operation portion 3 and a universal cable 4. Other components are similar to those of the first embodiment described above.

Note that, in FIG. 5, reference symbol OPL2 indicates an optical path length of a light flux led to the second image pickup device 32. Reference symbol OPL1 indicates an optical path length of a light flux led to the first image pickup device 31. Reference symbol OPL1a indicates an optical path length of a light flux led to the third image pickup device 47.

Here, the optical path length OPL1a of a nearest neighbor, the optical path length OPL1 of a near point and the optical path length OPL2 of a far point are set so that OPL1a>OPL1>OPL2 is satisfied.

That is, the third image pickup device 47 arranged on a side for which a setting is made so that a relatively longest optical path length (OPL1a) is obtained is an image pickup device for the nearest neighbor capable of obtaining an image for the nearest neighbor (an image in which a subject 101ka existing at the nearest neighbor is focused).

Further, the first image pickup device 31 arranged on a side for which a setting is made so that an optical path length longer than the optical path length OPL2 (OPL1) is obtained is an image pickup device for the near point capable of obtaining an image for the near point, that is, an image in which a subject 101k existing at the near point is focused.

The second image pickup device 32 arranged on a side for which a setting is made so that a relatively shortest optical path length (OPL2) is obtained is an image pickup device for the far point capable of obtaining an image for the far point, that is, an image in which a subject 101e existing at the far point is focused.

Further, in the present embodiment also, a quantity of light which enters each of the image pickup devices (31, 32 and 47) is adjusted on the basis of settings of reflectances of the first and second half mirror planes 36 and 56. That is, the reflectances of the first and second half mirror planes 36 and 56 are set such that the quantity of light to each of the image pickup devices (31, 32 and 47) satisfies: for a far point (32)>for a near point (31)>for a nearest neighbor (47).

In the endoscope apparatus of the present embodiment configured as described above, it is possible to simultaneously acquire three image signals using the three image pickup devices 31, 32 and 47. The three images are images which are set such that an appropriate focused state is obtained according to a distance to a subject. Similarly to the first embodiment described above, comparison among contrasts of the three images is automatically performed by a processor unit 20 (see FIG. 3), and such control is performed that an image signal with a highest contrast is selected and outputted to a display device 21. Thereby, an appropriate image is automatically displayed on the display device 21.

As described above, according to the third embodiment, it is possible to obtain advantages similar to those of each embodiment described above. Furthermore, according to the present embodiment, a configuration is made in which the objective lens 33C, which is a zoom-lens-type photographing optical system, is applied, and the three image pickup devices 31, 32 and 47 are provided so that three images can be obtained according to distances to subjects. Therefore, it becomes possible to obtain an image with a wider depth of field.

Fourth Embodiment

Next, a fourth embodiment of the present invention will be described. A configuration of the present embodiment is basically almost similar to that of the first embodiment described above but is slightly different only in a configuration of an objective lens constituting an image pickup optical system of an image pickup unit. Therefore, components similar to those of the first embodiment described above are given same reference symbols, and detailed description thereof will be omitted. Only different parts will be described below.

Figure 6:
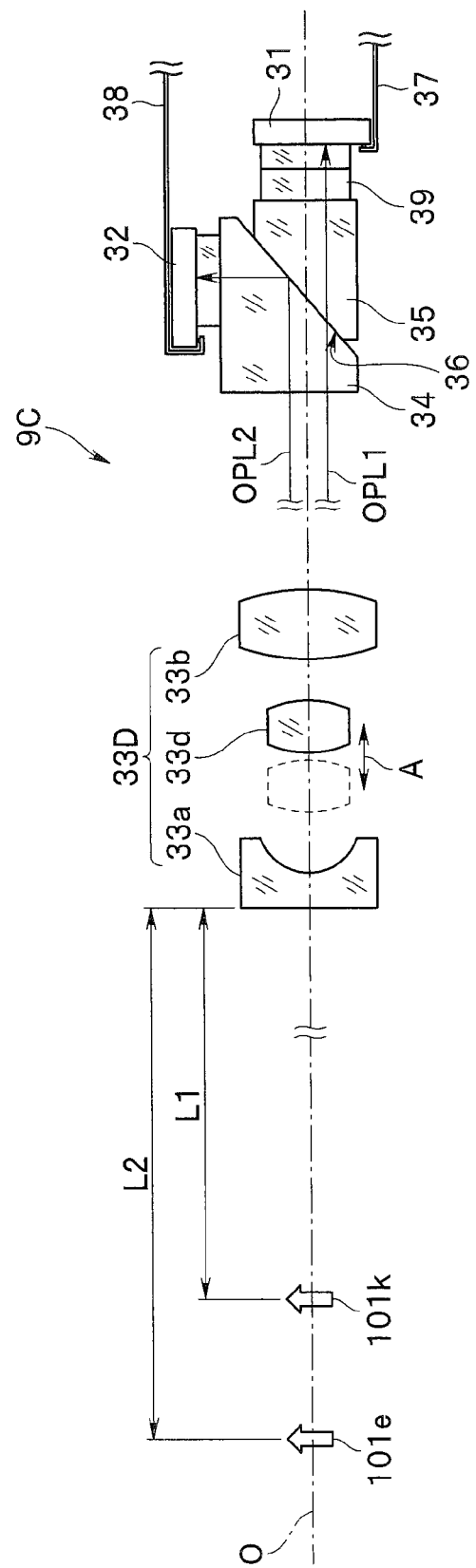
FIG. 6 is a diagram showing an outline of an image pickup unit in an endoscope apparatus of a fourth embodiment of the present invention.

FIG. 6 is a diagram showing an outline of the image pickup unit in an endoscope apparatus of the fourth embodiment of the present invention. As shown in FIG. 6, in an image pickup unit 9C in the endoscope apparatus of the present embodiment, an objective lens of a type capable of adjusting a focus is applied as an objective lens 33D, which is an image pickup system. The objective lens 33D is configured with a first lens 33a and a second lens 33b fixedly arranged in the image pickup unit 9C, a plurality of optical lens groups, such as a focus lens system 33d which is a movable lens arranged to freely move forward and backward in an optical axis O direction (a direction of an arrow A shown in FIG. 6) relative to the first lens 33a and the second lens 33b, driving means constituted by a driving mechanism and a driving source (neither of them is shown) for appropriately causing the focus lens system 33d to move forward or backward in the optical axis O direction on the basis of a predetermined operation instruction (a manual operation instruction or an automatic operation instruction), and the like. In this case, the driving means causes the focus lens system 33d (a movable lens) to move so that a difference among contrasts of images based on output image signals of the plurality of image pickup devices (31, 32 and 47) becomes largest. The difference among the contrasts in this case is a difference among peak values of the contrasts of images based on the respective image signals.

Two kinds of image signals are outputted from the respective two image pickup devices 31 and 32 of the image pickup unit 9C configured as described above. These output signals (image signals) are transmitted to the processor unit similarly to the first embodiment described above. In response to input of the image signals, the processor unit executes necessary image processing.

Figure 7:
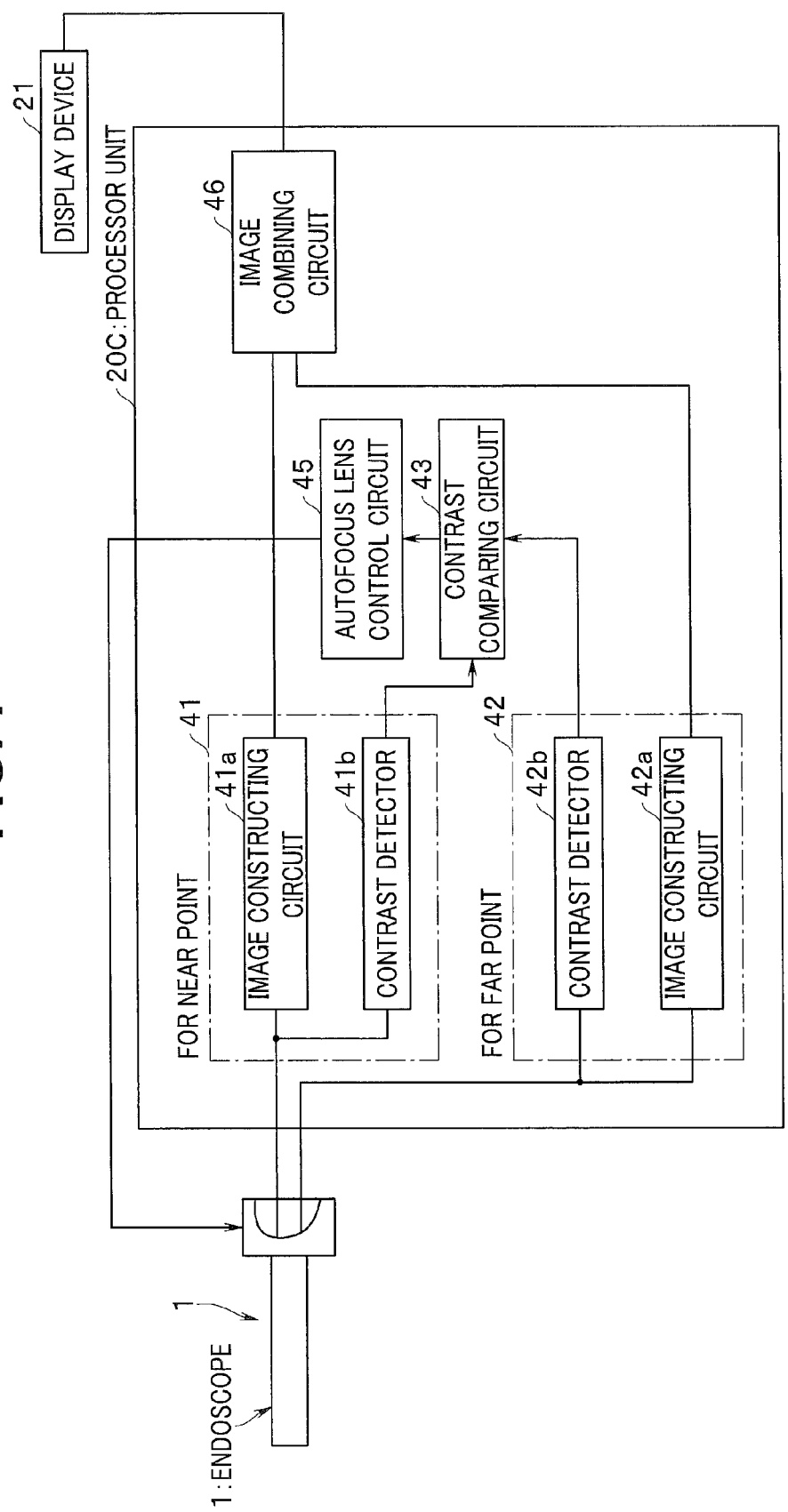
FIG. 7 is a block configuration diagram showing only (image-processing-circuit-related) components related to the present invention in an internal configuration of a processor unit in the endoscope apparatus of FIG. 6.

Here, an image-processing-circuit-related configuration in an internal configuration of the processor unit in the present embodiment will be described briefly. FIG. 7 is a block configuration diagram showing only the (image-processing-circuit-related) components related to the present invention in the internal configuration of the processor unit in the endoscope apparatus of the present embodiment.

As shown in FIG. 7, a processor unit 20C in the endoscope apparatus of the present embodiment is provided with an image processing circuit 41 for a near point, an image processing circuit 42 for a far point, a contrast comparing circuit 43, an autofocus lens control circuit 45, an image combining circuit 46 and the like. Among these, each of the image processing circuits 41 and 42, and the contrast comparing circuit 43 are circuit units having configurations and functions similar to those of the first embodiment described above.

The autofocus lens control circuit 45 is a circuit unit which, by performing driving control of a focus driving source (not shown) provided, for example, in an operation portion 3 of an endoscope 1, performs driving control for causing the focus lens system 33d of the objective lens 33D of the image pickup unit 9C to move forward or backward on an optical axis O. The autofocus lens control circuit 45 executes control of an autofocus operation in response to an output from the contrast comparing circuit 43 (a contrast comparison result).

Note that, separately from this, the autofocus lens control circuit 45 is also adapted to perform control for an automatic focus adjusting operation (an autofocus operation) in response to an autofocus instruction signal which occurs, for example, by a predetermined operation portion included among operation members 15 provided on the operation portion 3 being operated.

The image combining circuit 46 is a circuit unit which, in response to an output from the image constructing circuit 41a for a near point and an output from the image constructing circuits 42a for a far point, performs an image combining process for extracting image areas satisfying a predetermined condition, that is, images area with a high contrast and generating one image signal.

Note that, in the present embodiment, the image switching switch 44 is not provided unlike the first embodiment described above (see FIG. 3). Other components are similar to those of the first embodiment described above.

As described above, according to the fourth embodiment described above, advantages similar to those of the first embodiment described above can be also obtained in the endoscope apparatus adopting the image pickup unit 9C to which the objective lens 33D, which is a photographing optical system of a type capable of adjusting a focus, is applied. Furthermore, according to the present embodiment, since it is possible to adjust a focus for a desired part of a subject, it is possible to easily cause an image with a high contrast to be formed more clearly.

The processor unit 20 in the first to third embodiments described above is configured to, in response to output signals from a plurality of image pickup devices, perform control for selectively displaying an image with a high contrast. In comparison therewith, in the present embodiment, the processor unit 20C is adapted to, in response to a plurality of output signals (in this example, an image signal for a near point and an image signal for a far point) from a plurality of image pickup devices, perform the image combining process for extracting an image area with a high contrast in each image to generate one image signal and perform control to cause the display device 21 to automatically display the combined image. Therefore, it is possible to generate and display an image with a wider depth of field.

Fifth Embodiment

Next, a fifth embodiment of the present invention will be described. A configuration of the present embodiment is basically almost similar to that of each embodiment described above. For example, a configuration of an objective lens constituting an image pickup optical system of an image pickup unit is similar to the configuration of the first embodiment described above. Further, a configuration in which four prisms are provided behind the objective lens along an optical axis O direction in the image pickup unit, and each of three image pickup devices is arranged at a predetermined position is almost similar to that of the third embodiment. Therefore, components similar to those of each embodiment described above are given same reference symbols, and detailed description thereof will be omitted. Only different parts will be described below.

Figure 8:
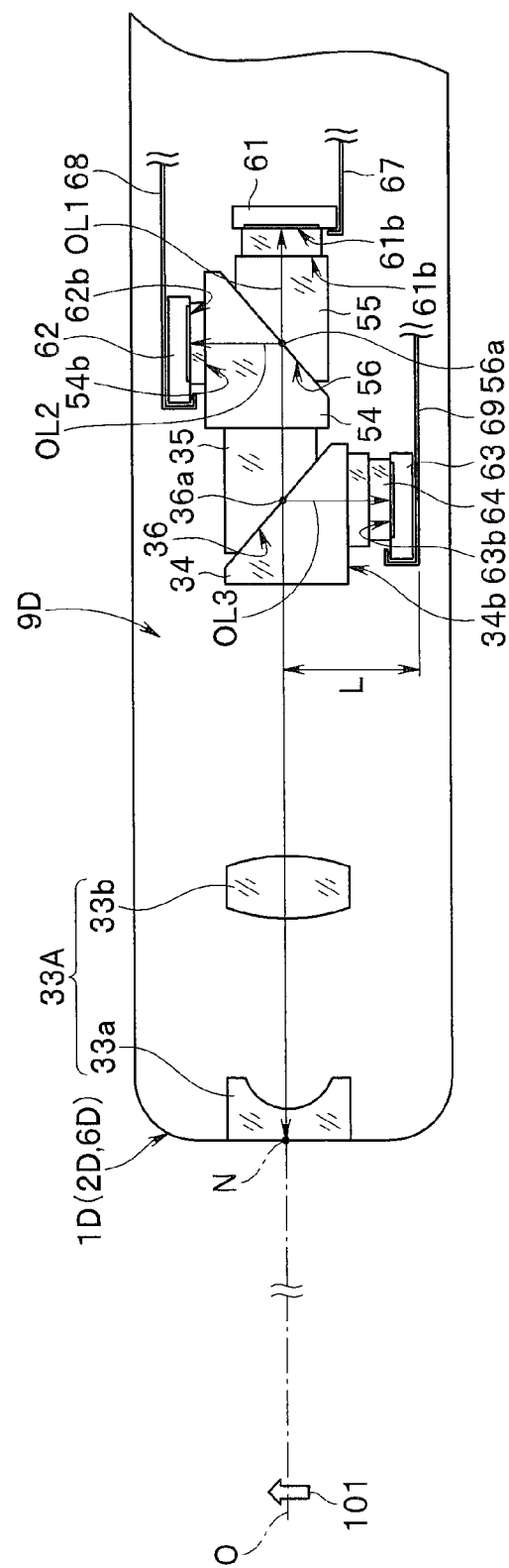
FIG. 8 is a diagram showing an outline of an image pickup unit in an endoscope apparatus of a fifth embodiment of the present invention.

FIG. 8 is a diagram showing an outline of the image pickup unit in the endoscope apparatus of the fifth embodiment of the present invention. As shown in FIG. 8, an image pickup unit 9D arranged inside a distal end portion 6D of an insertion portion 2D of an endoscope 1D in the endoscope apparatus of the present embodiment is configured with an objective lens 33A, two prism units constituted by four prisms (34, 35, 54 and 55) provided on an optical axis O of the objective lens 33A and behind the objective lens 33A, three image pickup devices (61, 62 and 63) provided on planes of emission of respective predetermined prisms, flexible printed circuits (FPCs) 67, 68 and 69 extended from the three image pickup devices (61, 62 and 63), respectively, a high-refractive optical device 64 arranged facing a light receiving plane 63b of an image pickup device arranged nearest to the objective lens 33A among the three image pickup devices (in this example, the sixth image pickup device 63; to be described later), and the like.

The four prisms are the first prism 34, the second prism 35, the third prism 54 and the fourth prism 55 arranged in that order from a side near to the objective lens 33A, similarly to the third embodiment described above. A configuration and arrangement of each of the four prisms are almost similar to those of the third embodiment described above.

Note that, in the present embodiment, the first and second prisms 34 and 35 on a front side, among the four prisms, are referred to as a first prism unit, and the third and fourth prism 54 and 55 on a back side are referred to as a second prism unit. Here, the first prism unit is arranged behind the objective lens 33A, and it divides a light flux from the objective lens 33A into two on a first half mirror plane 36 of the first prism 34, which is optical path dividing means, and leads one light flux to the fourth image pickup device 61 (corresponding to the first image pickup device in each of the embodiments described above) while leading the other light flux backward. That is, the first half mirror plane 36 of the first prism 34 has a function of dividing an incident light into two similarly to each of the embodiments described above.

On the other hand, the second prism unit is arranged behind the first prism unit, and it performs color separation of the other light flux led backward from the first prism unit by the third prism 54, which is optical path dividing means, and leads respective light fluxes separated thereby to the fifth image pickup device 62 (corresponding to the second image pickup device in each of the embodiments described above) and the sixth image pickup device 63 (corresponding to the third image pickup device in each of the embodiments described above). As the second half mirror plane 56 of the third prism 54, a dichroic optical system for performing color separation of an incident light is adopted.

In the present embodiment, the second half mirror plane 56 reflects only a green component light (a luminance component) of an incident light which enters the third prism 54 after being transmitted through the first and second prisms 34 and 35 and leads the green component light to a direction orthogonal to the optical axis O and opposite to a direction of bending the light flux by the half mirror plane 36 of the first prism 34 (a light receiving plane 62b of the fifth image pickup device 62 to be described later) while transmitting a remaining light flux in a direction along the optical axis O (backward).

The three image pickup devices are the sixth image pickup device 63 which acquires an image signal for a special observation image, the fourth image pickup device 61 and the fifth image pickup device 62 which acquire an image signal for a normal observation image.

That is, in the configuration of the present embodiment, by providing three image pickup devices for the image pickup unit 9D, two images, the special observation image and the normal observation image excellent in color reproduction, can be simultaneously acquired.

Therefore, one of the three image pickup devices is, for example, the sixth image pickup device 63 which acquires an image signal indicating a special observation image, such as fluorescence observation and infrared light observation images. The sixth image pickup device 63 is arranged such that its light receiving plane 63b faces a plane of emission 34b of the first prism 34. The high-refractive optical device 64 is arranged being sandwiched between the plane of emission 34b of the first prism 34 and the sixth image pickup device 63 (corresponding to the third image pickup device in each of the embodiments described above).

Here, when a transparent device is applied as the high-refractive optical device 64, and a highly-sensitive device is adopted as the sixth image pickup device 63, fluorescence of a living body can be detected, and, therefore, the sixth image pickup device 63 can output an image signal for fluorescence observation.

Further, when an optical filter which transmits a particular wavelength is applied as the high-refractive optical device 64 and a device corresponding to a wavelength transmitted through the high-refractive optical device 64 is adopted as the sixth image pickup device, high sensitivity to the particular wavelength can be obtained. Therefore, for a particular wavelength, for example, for an infrared light, the sixth image pickup device 63 can output an image signal for infrared light observation.

Note that, by arranging the high-refractive optical device 64 at the particular part described above (between the plane of emission 34b of the first prism 34 and the sixth image pickup device 63), an optical path length L after a light is reflected and bent by the first half mirror plane 36 (see FIG. 8) among optical path lengths can be shortened. That is, by providing the high-refractive optical device 64, it is possible to suppress upsizing of the distal end portion 6D in the endoscope 1D.

On the other hand, the other two among the three image pickup devices are image pickup devices for acquiring an image signal indicating a normal observation image. One of them is the fourth image pickup device 61 which acquires red and green component lights (image constructing components), and the other one is the fifth image pickup device 62 which acquires a green component light (a luminance component).

On the other hand, the fourth image pickup device 61 is arranged so that its light receiving plane 61*b* faces a plane of emission 55*b* of the fourth prism 55. The fifth image pickup device 62 is arranged so that its light receiving plane 62*b* faces a plane of emission 54*b* of the third prism 54.

In the configuration in the present embodiment, a length OL1 of an optical path from a front position N of the first lens 33*a* (see FIG. 8) to the light receiving plane 61*b* of the fourth image pickup device 61 and a length OL2 of an optical path from the front position N of the first lens 33*a* to the light receiving plane 62*b* of the fifth image pickup device 62 are set to be equal to each other (OL1=OL2). Furthermore, a length OL3 of an optical path from the front position N of the first lens 33*a* to the light receiving plane 63*b* of the sixth image pickup device 63 is also set to be equal to the lengths OL1 and OL2 of the optical paths (OL1=OL2=OL3).

Further, a pair of the image pickup devices 62 and 63 whose light receiving planes are arranged parallel to the plane along the optical axis O are arranged such that planes which include the light receiving planes 62*b* and 63*b* substantially face each other with the optical axis O between the planes. By adopting the configuration, it does not happen that peripheral configuration members around the image pickup devices, such as the flexible printed circuits (FPCs) 68 and 69 extended from the image pickup devices 62 and 63, respectively, interfere, so that it is possible to improve efficiency of arrangement of the members. Note that the pair of image pickup devices arranged facing each other is not limited to the combination (62 and 63) described above.

In the image pickup unit 9D in the endoscope 1D configured as described above, three image signals are simultaneously outputted from the three image pickup devices (61, 62 and 63). The output signals (image signals) are inputted to a processor unit (20). In this case, by predetermined processing being performed by an image processing circuit for the image signal of the fourth image pickup device 61 (an image signal generated based on a green component light) and the image signal of the fifth image pickup device 62 (an image signal generated based on a green component light) among the three image signals, an image signal for normal observation are generated. On the other hand, predetermined processing is performed for the remaining image signal, that is, the image signal of the sixth image pickup device 63, and an image signal for a special image is generated.

Output switching is performed between the two image signals generated in this way (the respective image signals for normal observation and for special observation) in response to an instruction signal from a predetermined operation member 15 provided for an operation portion 3, and either one of the two image signals is outputted to and displayed on the display device 21. Other components are almost similar to those of the first or third embodiment described above.

As described above, according to the fifth embodiment described above, it is possible to obtain advantages almost similar to those of each embodiment described above. Furthermore, in the present embodiment, by applying an image pickup device corresponding to a wavelength of a special light as the sixth image pickup device 63, it is possible to realize an image pickup unit compatible with various wavelengths and configure an endoscope apparatus to which the image pickup unit is applied.

Further, by arranging the plurality of image pickup devices (61, 62 and 63) in a well-balanced state relative to the optical axis O, it is possible to prevent the flexible printed circuit extended from each image pickup device and the like from interfering and contribute to downsizing of the whole endoscope apparatus by an efficient internal layout.

Since the high-refractive optical device 64 is arranged near the sixth image pickup device 63 arranged at a position nearest to the objective lens 33A, that is, near the light receiving plane 63*b*, it is possible to suppress upsizing of the image pickup unit 9D itself, and it is possible to set the lengths of the optical paths to the three respective image pickup devices (61, 62 and 63) so that OL1=OL2=OL3 is satisfied.

Further, since two image signals are generated by performing color separation of an incident light flux, causing one of divided light fluxes (a green component light) to enter the fourth image pickup device 61 and causing the other (a red and green component light) to the fifth image pickup device 62, and predetermined image processing is performed for the image signals at the processor unit (20), it is possible to realize an endoscope apparatus which acquires a normal observation image excellent in color reproduction.

Note that, though, in the present embodiment, the configuration of the objective lens 33A constituting the image pickup optical system of the image pickup unit 9D is similar to that of the first embodiment, the configuration is not limited thereto, and the zoom-type objective lens in the second and third embodiments described above, the objective lens of the type capable of adjusting a focus in the fourth embodiment or the like may be applied.

Further, in the present embodiment, though the configuration is made by causing the respective light receiving planes 62*b* and 63*b* of the two image pickup devices 62 and 63, which are arranged parallel to the plane along the optical axis O, to be arranged so that the light receiving planes 62*b* and 63*b* substantially face each other with the optical axis O therebetween, the configuration is not limited thereto.

As another arrangement example, for example, an arrangement is also possible in which the respective light receiving planes 62*b* and 63*b* of the two image pickup devices 62 and 63 adjoin each other. In this case, bending directions of light fluxes from the optical axis O can be set to the same direction by causing an inclination direction of the first half mirror plane 36 to correspond to an inclination direction of the second half mirror plane 56.

Furthermore, in addition to the arrangement example, it is also possible to arrange the two image pickup devices 62 and 63, for example, at positions away from each other by an angle of about 90 degrees around the optical axis O. The arrangement angle around the optical axis in this case is not limited to about 90 degrees but can be arbitrarily set within an angle range of 0 to 180 degrees in consideration of an internal layout of the distal end portion 6D of the endoscope 1D. Thereby, it is possible to improve efficiency of arrangement of members more.

Sixth Embodiment

Next, a sixth embodiment of the present invention will be described. A configuration of the present embodiment is basically almost similar to that of each embodiment described above but is different in a point that an objective lens as an image pickup optical system is configured in a form suitable for generation of a 3D image. Therefore, components similar to those of each embodiment described above are given same reference symbols, and detailed description thereof will be omitted. Only different parts will be described below.

Figure 9:
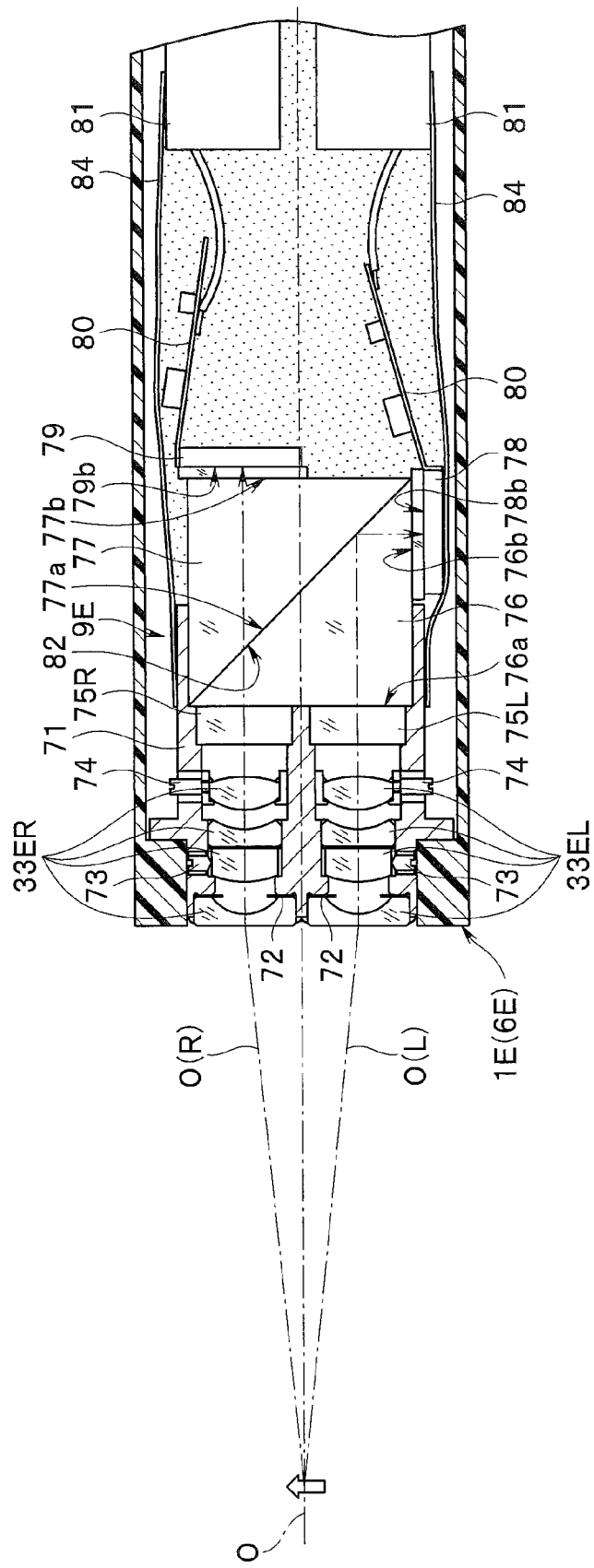
FIG. 9 is a diagram showing an outline of an internal configuration of a distal end portion of an insertion portion of an endoscope in an endoscope apparatus of a sixth embodiment of the present invention.
Figure 10:
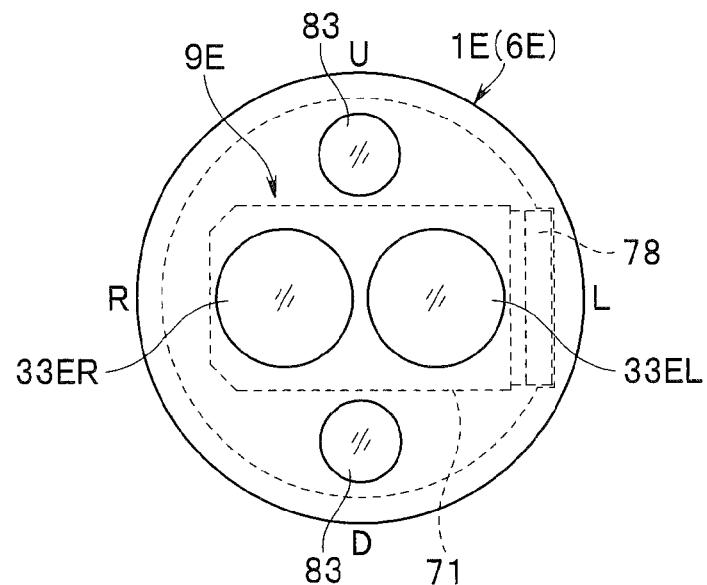
FIG. 10 is a schematic front view when the distal end portion of the insertion portion of the endoscope of FIG. 9 is seen from a front.
Figure 11:
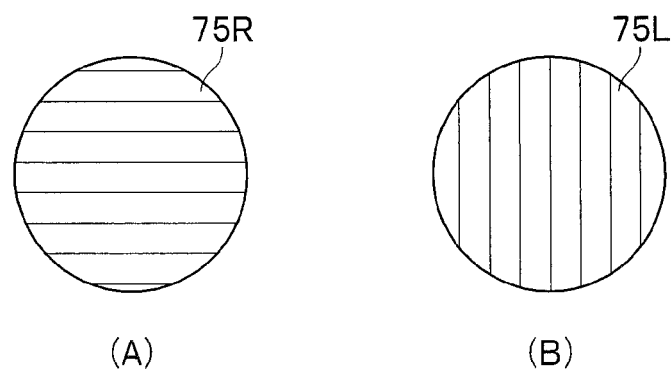
FIG. 11 is a schematic diagram showing a schematic shape of a polarization filter applied to an image pickup unit of the endoscope apparatus of FIG. 9.

FIG. 9 is a diagram showing an outline of an internal configuration of a distal end portion of an insertion portion of an endoscope in an endoscope apparatus of the sixth embodiment of the present invention. FIG. 10 is a schematic front view when the distal end portion of the insertion portion of the endoscope of FIG. 9 is seen from a front. FIG. 11 is a schematic diagram showing a schematic shape of a polarization filter applied to the image pickup unit of the endoscope apparatus of FIG. 9.

As shown in FIG. 9, an image pickup unit 9E is fixedly arranged inside a distal end portion 6E of an insertion portion of an endoscope 1E.

The image pickup unit 9E is mainly configured with: objective lens units each of which is prepared as a pair (objective lenses 33ER and 33EL, or the like) for a three-dimensional image (a stereo image; a 3D image); a prism unit (76 and 77, or the like) provided behind the objective lens units; two polarization filters (75R and 75L) provided on planes of incidence of the prism units; two image pickup devices (78 and 79) provided on a plurality of planes of emission of the prism units, respectively; and flexible printed circuits (FPCs) 80 extended from the two respective image pickup devices; and the like.

The objective lens unit has the first objective lens 33ER for forming an image for a right eye and the second objective lens 33EL for forming an image for a left eye. Here, the second objective lens 33EL is arranged parallel to a subject to be provided with parallax relative to the first objective lens 33ER. In other words, the first objective lens 33ER and the second objective lens 33EL are formed side by side in a horizontal direction of the endoscope 1E. Here, the horizontal direction of the endoscope 1E is a direction corresponding to a horizontal direction of an endoscopic image which is outputted and displayed by the endoscope apparatus in the end.

Each of the first objective lens 33ER and the second objective lens 33EL is configured with a plurality of optical lenses. Further each of the plurality of optical lenses constituting each of the first objective lens 33ER and the second objective lens 33EL is fixedly arranged inside a lens barrel 71 formed in a cylindrical shape.

Note that a part of the plurality of optical lenses constituting each of the first objective lens 33ER and the second objective lens 33EL can be adjusted by a deviation angle/core adjustment screw 73 and are in a state of being movable relative to the lens barrels 71. Similarly, the other part of the optical lenses can be adjusted by a focus adjustment pin 74 and are in a state of being movable relative to the lens barrels 71. Therefore, each of the first objective lens 33ER and the second objective lens 33EL is configured to be adjustable by the deviation angle/core adjustment screw 73 and the focus adjustment pin 74 so that appropriate two images can be formed at appropriate positions in appropriate states. Note that these adjustment mechanisms are parts which are not directly related to the present invention, and detailed description thereof will be omitted on assumption that a configuration which conventionally has been generally practically used is applied.

Further, a diaphragm plate 72 for restricting a quantity of incident light from frontward is arranged at a predetermined position of an optical path of the plurality of optical lenses constituting each of the first objective lens 33ER and the second objective lens 33EL.

The two polarization filters (75R and 75L) are a pair of polarization filters whose polarization directions cross each other. Between the two, the first polarization filter 75R, which is a first optical filter, is arranged on an optical axis O(R) of the first objective lens 33ER and behind the first objective lens 33ER. That is, the first polarization filter 75R is arranged in contact with a plane of incidence 76a of the first prism 76 (to be described later) of the prism unit. Here, the optical axis O(R) of the first objective lens 33ER and a central axis of the first polarization filter 75R are set to substantially correspond to each other. The first polarization filter 75R is formed so as to be able to cause only a vertical direction component V of an incident light to be transmitted (see FIG. 11(A)).

Similarly, the second polarization filter 75L, which is a second optical filter, is arranged on an optical axis O(L) of the second objective lens 33EL and behind the second objective lens 33EL. That is, the second polarization filter 75L is arranged in contact with the plane of incidence 76a of the first prism 76 (to be described later) of the prism unit. Here, the optical axis O(L) of the second objective lens 33EL and a central axis of the second polarization filter 75L are set to substantially correspond to each other. The second polarization filter 75L is constituted by a filter of a kind different from the first polarization filter 75R and is formed so as to be able to cause only a horizontal direction component H of an incident light to be transmitted (see FIG. 11(B)).

The prism unit is configured with two prisms, the first prism 76 and the second prism 77. The first prism 76 is optical path dividing means for, when a light flux transmitted through the two polarization filters 75R and 75L comes in, dividing the incident light in two predetermined directions, and the first prism 76 is a half prism. Therefore, the first prism 76 is formed being provided with the plane of incidence 76a, a polarization beam splitter plane 82 and a plane of emission 76b.

The plane of incidence 76a of the first prism 76 is constituted by a plane orthogonal to each of the optical axes O(R) and O(L) of the first objective lens 33ER and the second objective lens 33EL, and the two polarization filters (75R and 75L) are arranged on extensions of the respective optical axes O(R) and O(L).

The polarization beam splitter plane 82 of the first prism 76 is formed having an inclination angle of about 45 degrees relative to the plane of incidence 76a. Thereby, the polarization beam splitter plane 82 divides an incident light which has entered from the plane of incidence 76a in a direction orthogonal to the optical axes O(R) and O(L) and a direction along the optical axes O(R) and O(L). That is, the polarization beam splitter plane 82 causes a light flux (a vertical direction component V) which has been transmitted through the first polarization filter 75R after being transmitted through the first objective lens 33ER and has entered from the plane of incidence 76a of the first prism 76 to pass through. The light flux enters the second prism 77 at the back.

On the other hand, the polarization beam splitter plane 82 reflects a light flux (a horizontal direction component H) which has been transmitted through the second polarization filter 75L after being transmitted through the second objective lens 33EL and has entered from the plane of incidence 76a of the first prism 76, emits the light flux from the plane of emission 76b, bending its optical path by an angle of about 90 degrees, and causes the light flux to enter a light receiving plane 78*b* of an image pickup device 78 for a left eye (a second image pickup device).

The plane of emission 76*b* is formed having a plane orthogonal to the light flux after being bent by the polarization beam splitter plane 82. The image pickup device 78 for a left eye to be described later is arranged on the plane of emission 76*b*.

The second prism 77 is formed having a plane of incidence 77*a* formed to be in contact with the polarization beam splitter plane 82 of the first prism 76, a plane of emission 77*b* constituted by a plane orthogonal to the optical axes O(R) and O(L) of the first objective lens 33ER and the second objective lens 33EL, respectively. An image pickup device 79 for a right eye (a first image pickup device) to be described later is arranged on the plane of emission 77*b*.

The two image pickup devices are the image pickup device 79 for a right eye, which is the first image pickup device having a light receiving plane 79*b* which receives a light flux having passed through the first objective lens 33ER, and the image pickup device 78 for a left eye, which is the second image pickup device having the light receiving plane 78*b* which receives a light flux having passed through the second objective lens 33EL.

On the image pickup device 79 for a right eye, the light receiving plane 79*b* is arranged facing the plane of emission 77*b* of the second prism 77. Thereby, the image pickup device 79 for a right eye receives a light flux having passed through the first objective lens 33ER. That is, as described above, the first polarization filter 75R is arranged between the first objective lens 33ER and the image pickup device 79 for a right eye. Further, the polarization beam splitter plane 82 of the first prism 76 is arranged between the first polarization filter 75R and the image pickup device 79 for a right eye. Due to such a configuration, the image pickup device 79 for a right eye receives a light flux of a vertical direction component V in an incident light.

On the other hand, on the image pickup device 78 for a left eye, the light receiving plane 78*b* is arranged facing the plane of emission 76*b* of the first prism 76. Thereby, the image pickup device 78 for a left eye receives a light flux having passed through the second objective lens 33EL. That is, as described above, the second polarization filter 75L is arranged between the second objective lens 33EL and the image pickup device 78 for a left eye. Further, the polarization beam splitter plane 82 of the first prism 76 is arranged between the second polarization filter 75L and the image pickup device 78 for a left eye. Due to such a configuration, the image pickup device 78 for a left eye receives a light flux of a horizontal direction component H in an incident light.

From each of the two image pickup devices 78 and 79, the flexible printed circuit (FPC) 80 extends backward. A signal cable 81 which is inserted through an insertion portion, an operation portion and a universal cable and reaches the processor unit 20 in the end via an endoscope connector is electrically connected to each flexible printed circuit (FPC) 80. An outer circumference on a back end side of the lens barrel 71 and an outer circumference on a distal end side of the signal cable 81 are coupled via a heat-shrinkable tube 84, in which adhesive is filled to fix internal components (the flexible printed circuit 80 and the like).

Note that optical path lengths of the first objective lens 33ER and the second objective lens 33EL in the image pickup unit 9E are set to be equal to each other.

Further, in the front view shown in FIG. 10, two illuminating windows 83 of an illumination optical system are provided near each of the first objective lens 33ER and the second objective lens 33EL. A distal end of a light guide inserted inside the insertion portion 2, the operation portion 3 and the universal cable 4 is connected to the illuminating windows 83, and a configuration is made so that an illuminating light transmitted from the light source device 22 via the light guide is emitted toward a subject ahead from the illuminating windows 83. Other components are almost similar to those of each of the embodiments and the like.

Figure 13:
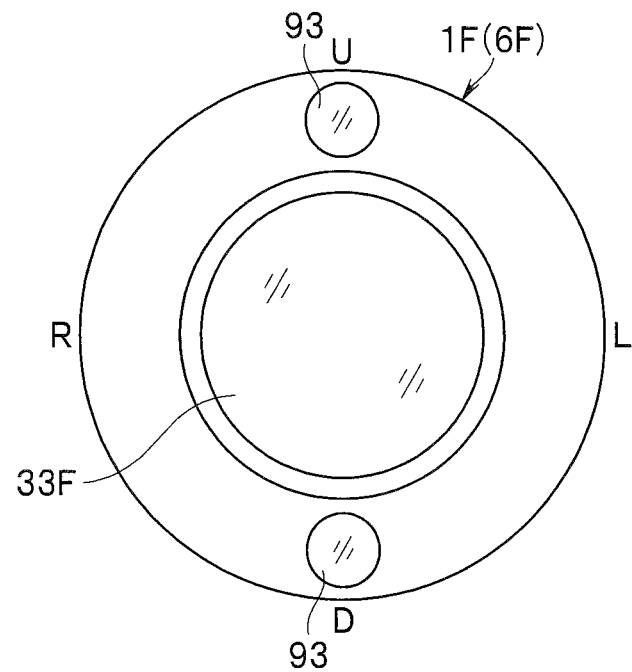
FIG. 13 is a schematic front view when the distal end portion of the insertion portion of the endoscope of FIG. 12 is seen from a front.

Note that reference symbols R, L, D and U shown in FIG. 10 indicate directions at a time when the endoscope itself exists at a proper position, and reference symbol R indicates a right direction of the endoscope (a right side of an endoscopic image). Reference symbol L indicates a left direction of the endoscope (a left side of an endoscopic image). Here, the right and left of the endoscope refer to the right and left direction when seen from the user. Since FIG. 13 shows a case where the endoscope is seen from a front thereof, the right and left are shown opposite. Reference symbol D indicates a downward direction of the endoscope (a lower side of an endoscopic image). Reference symbol U indicates an upward direction of the endoscope (an upper side of an endoscopic image).

In the endoscope apparatus of the present embodiment configured as described above, two image signals acquired by the two image pickup devices 78 and 79 of the image pickup unit 9E are outputted to the processor unit (20). In response thereto, the processor unit (20) performs predetermined image processing to generate an image signal for display in a form which can be observed as a three-dimensional image and outputs the image to the display device (21). The image can be observed as a 3D image, for example, by performing monitor observation using polarization glasses.

As described above, according to the sixth embodiment, a configuration is made so as to cause one of two incident lights from the respective first objective lens 33ER and second objective lens 33EL to travel straight and cause the other to be reflected by a prism unit so that its optical path is bent by an angle of 90 degrees, and a configuration is made by arranging the image pickup device 79 for a right eye (the first image pickup device) and the image pickup device 78 for a left eye (the second image pickup device) in advancing directions of the respective light fluxes.

Thus, since a form of constituting planes of emission by different planes of a prism unit and providing an image pickup device on each of the planes of emission is adopted, it is not necessary to arrange the two image pickup device 78 and 79 side by side in a direction orthogonal to the optical axis of the objective optical system due to the configuration. Therefore, according to the configuration of the present embodiment, it is possible to contribute to downsizing of the image pickup unit 9E in a diameter direction and, as a result, contribute to downsizing of the distal end portion of the endoscope to which the configuration is applied. At the same time, it is possible to increase the size of each image pickup device while preventing upsizing of the image pickup unit itself, and, therefore, it becomes possible to easily improve image quality of an acquired image.

Since it is possible to configure and unitize the two image pickup devices in a form of being joined to one prism unit, it is possible to realize downsizing of the image pickup unit and downsizing of the endoscope itself to which the image pickup unit is applied, and, at the same time, it is possible to contribute to simplification of workability in a manufacturing process as well as improvement of assemblability. Furthermore, an advantage is also obtained that, by unitization of the image pickup devices and the prism unit by integration of the image pickup devices and the prism unit, necessity of adjusting two objective optical systems separately is eliminated.

Seventh Embodiment

Next, a seventh embodiment of the present invention will be described. A configuration of the present embodiment is basically almost similar to that of the sixth embodiment described above but is different in a point that an endoscope apparatus is compatible with a 3D image, and that an objective lens as an image pickup optical system is configured in a different form. Therefore, components similar to those of each embodiment described above are given same reference symbols, and detailed description thereof will be omitted. Only different parts will be described below.

Figure 12:
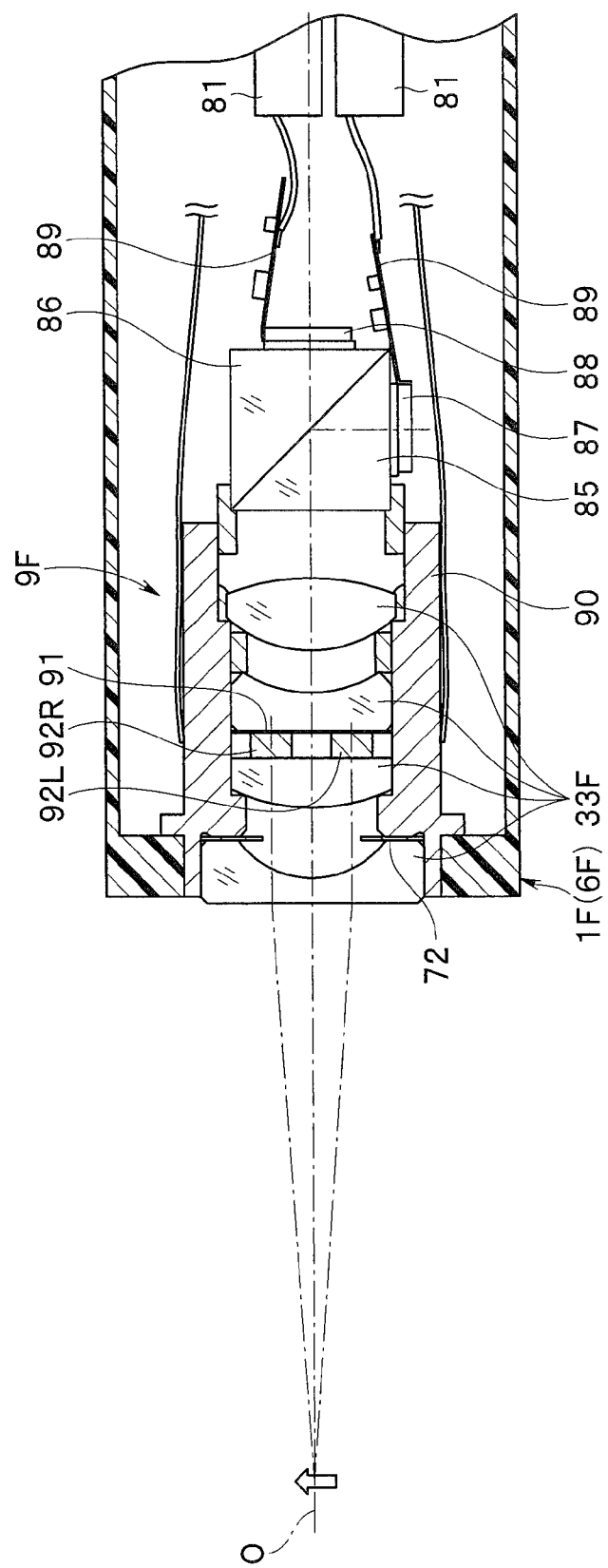
FIG. 12 is a diagram showing an outline of an internal configuration of a distal end portion of an insertion portion of an endoscope in an endoscope apparatus of a seventh embodiment of the present invention.
Figure 14:
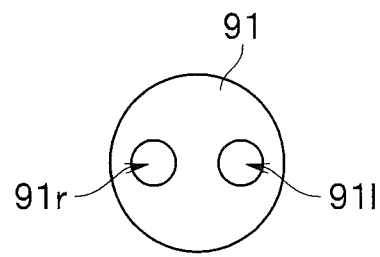
FIG. 14 is a front view showing a schematic shape of a visual field diaphragm plate applied to an image pickup unit of the endoscope apparatus of FIG. 12.

FIG. 12 is a diagram showing an outline of an internal configuration of a distal end portion of an insertion portion of an endoscope in the endoscope apparatus of the seventh embodiment of the present invention. FIG. 13 is a schematic front view when the distal end portion of the insertion portion of the endoscope of FIG. 12 is seen from a front. FIG. 14 is a front view showing a schematic shape of a visual field diaphragm plate applied to an image pickup unit of the endoscope apparatus of FIG. 12.

The sixth embodiment described above adopts a form in which two objective optical systems are provided to form two images. In comparison with the configuration, a configuration is made so that two images are formed by one objective optical system in the present embodiment.

That is, as shown in FIG. 12, an image pickup unit 9F is fixedly arranged inside a distal end portion 6F of an insertion portion of an endoscope 1F in the endoscope apparatus of the present embodiment.

The image pickup unit 9F is mainly configured with an objective lens unit (objective optical systems 33F or the like), a prism unit (85 and 86, or the like) provided behind the objective lens unit, two image pickup devices (87 and 88) provided on a plurality of planes of emission of the prism unit, respectively, a flexible printed circuit (FPC) 89 extending from each of the two image pickup devices, and the like.

The objective lens unit of the present embodiment is configured such that two images (for a right eye and for a left eye) for a three-dimensional image (a stereo image; a 3D image) are formed by one objective optical system. That is, the objective lens unit of the present embodiment is mainly configured with the objective optical systems 33F constituted by a plurality of optical lenses, a lens barrel 90 for fixing the objective optical systems 33F, a diaphragm plate 72 for restricting a quantity of incident light from frontward, a visual field diaphragm plate 91 which generates two light fluxes, a light flux for causing an image for a right eye to be formed and a light flux for causing an image for a left eye to be formed, from an incident light that has entered the objective optical systems 33F, polarization filters (92R and 92L), and the like.

The visual field diaphragm plate 91 is arranged at a middle position of the objective optical systems 33F as shown in FIG. 12. Further, as shown in FIG. 14, the whole visual field diaphragm plate 91 is formed in a disk shape, and two holes 91r and 91l which enables a light to pass through are formed, being punched at positions at a middle of a diameter of the disk with a central axis of the disk therebetween when seen from a front. A part of the visual field diaphragm plate 91 other than the two holes 91r and 91l are formed so as to prevent a light from passing through. Therefore, due to the configuration, a light flux which has entered from a front of the objective optical systems 33F is divided into two light fluxes and emitted backward by the visual field diaphragm plate 91. Further, the two holes 91r and 91l are formed side by side in a horizontal direction of the endoscope 1F. Here, the horizontal direction of the endoscope 1F is a direction corresponding to a horizontal direction of an endoscopic image which is outputted and displayed by the endoscope apparatus in the end. Thereby, two images formed by the objective optical systems 33F on the basis of the light fluxes which have passed through the two holes 91r and 91l are formed having parallax.

The polarization filters (92R and 92L) are fixedly arranged immediately before the holes 91r and 91l of the visual field diaphragm plate 91, respectively. The two polarization filters (92R and 92L) are a pair of polarization filters whose polarization directions cross each other. Between them, the first polarization filter 92R, which is a first optical filter, is fixedly arranged at a position immediately before the hole 91r for a right eye of the visual field diaphragm plate 91. The first polarization filter 92R is formed such that, for example, only a vertical direction component V of an incident light can be transmitted (see FIG. 11(A)).

Similarly, the second polarization filter 92L, which is a second optical filter, is fixedly arranged at a position immediately before the hole 91l for a left eye of the visual field diaphragm plate 91. The second polarization filter 92L is formed such that, for example, only a horizontal direction component H of an incident light can be transmitted (see FIG. 11(B)).

A configuration of the prism unit is almost similar to that of the sixth embodiment described above. That is, the first prism 85 is formed having a polarization beam splitter plane 82. Therefore, a light flux which has been transmitted through the first polarization filter 92R and has entered the first prism 85 (a vertical direction component V) passes through the polarization beam splitter plane 82, is transmitted through the second prism 86 at the back, enters a light receiving plane of the first image pickup device 88 for a right eye, and causes an image for a right eye to be formed on the light receive plane. On the other hand, a light flux which has been transmitted through the second polarization filter 92L and has entered the first prism 85 (the horizontal direction component H) is reflected by the polarization beam splitter plane 82, travels with its optical path bent by an angle of about 90 degrees, enters a light receiving plane of the second image pickup device 87 for a left eye, and causes an image for a right eye to be formed on the light receiving plane. In this case, optical path lengths of the two light fluxes described above are set to be equal to each other.

In a front view shown in FIG. 13, two illuminating windows 93 of an illumination optical system are provided near a peripheral edge side of the objective optical system 33F. A configuration of the illuminating windows 93 is similar to that of each of the embodiments described above, and the illuminating windows 93 are configured so as to emit an illuminating light transmitted via a light guide from a light source device 22 toward a subject existing ahead of the endoscope. Other components are almost similar to those of each of the embodiments described above. Note that reference symbols R, L, D and U shown in FIG. 13 are quite similar to those in FIG. 10 described in the sixth embodiment described above.

As described above, according to the seventh embodiment, in the endoscope apparatus to which the image pickup unit for stereoscopic view in a form of being configured so as to acquire two images having parallax by one objective optical system, it is possible to obtain advantages similar to those of the sixth embodiment described above.

By the embodiments of the invention described above, inventions configured as below can be obtained. That is:

(1) An image pickup unit including:
an objective lens;
a first prism unit arranged behind the objective lens, the first prism unit dividing a light flux from the objective lens and leading one light flux to a first image pickup device while leading the other light flux backward; and
a second prism unit arranged behind the first prism unit, the second prism unit performing color separation of the other light flux and leading each of light fluxes separated thereby to a second image pickup device and a third image pickup device.

(2) The image pickup unit according to the item (1), wherein an optical member with a high refractive index is arranged between the first prism unit and the first image pickup device.

(3) The image pickup unit according to the item (2), wherein the optical member with the high refractive index includes wavelength selecting means for causing only a light flux with a particular wavelength to be transmitted.

(4) The image pickup unit according to the item (1), wherein a pair of any two of the first image pickup device, the second image pickup device and the third image pickup device is arranged at positions where light receiving planes of the two image pickup devices face with each other.

(5) An endoscope apparatus using the image pickup unit according to the item (1).

Among conventional endoscope apparatuses, an endoscope apparatus provided with an image pickup unit in a special form of performing special-light observation has been practically used, in addition to, for example, an endoscope apparatus provided with an image pickup unit in a normal form of performing normal observation to acquire a color image. However, in order to make such a configuration that normal-light observation and special-light observation can be performed by one endoscope apparatus, it is necessary to cause a plurality of image pickup units, for example, a normal-observation image pickup unit excellent in color reproduction and a special-observation image pickup unit, to be included in a distal end portion of an insertion portion of a single endoscope. If such a configuration is adopted, an outer diameter of the distal end portion of the insertion portion of the endoscope apparatus increases. For recent endoscope apparatus, however, there is always a demand for downsizing of the apparatus itself, and, therefore, the configuration in which a plurality of image pickup units for different purposes are merely arranged is a form not to be adopted.

Therefore, there are proposed various kinds of endoscope apparatuses provided with a small-size image pickup unit which is configured, for example, so as to divide a light flux from an object transmitted through an objective lens using a dichroic prism or the like and lead the divided light fluxes to a plurality of image pickup devices, respectively, and which is devised to be compatible with various wavelengths by arranging a color filter or the like for transmitting only a light with a particular wavelength in an incident light on a light receiving plane of each image pickup device, for example, by Japanese Patent Application Laid-Open Publication No. 2007-50106.

The endoscope apparatus disclosed in Japanese Patent Application Laid-Open Publication No. 2007-50106 and the like is configured to divide a light flux which has passed through an image pickup optical system into a light with a wavelength of 500 nm or shorter and a light with a wavelength exceeding 500 nm by the dichroic prism and lead the former light with a wavelength of 500 nm or shorter to a first image pickup device via a first color filter, and the latter light with a wavelength exceeding 500 nm to a second image pickup device via a second color filter. During a normal-observation mode, a white color light is radiated to a subject, and a full-color normal-observation image is generated on the basis of image signals acquired by the two image pickup devices. On the other hand, during a special-observation mode, an excitation light is radiated to a subject via a blue filter; NBI system generates an image signal on the basis of an image signal acquired by the first image pickup device; and an autofluorescence image signal is generated on the basis of an image signal acquired by the second image pickup device. Due to the configuration, the endoscope apparatus disclosed by Japanese Patent Application Laid-Open Publication No. 2007-50106 and the like can appropriately switch between a normal-light observation image and a special-light observation image by a single image pickup unit, and, therefore, it is possible to realize downsizing of the endoscope apparatus.

Thus, since the endoscope apparatus disclosed by Japanese Patent Application Laid-Open Publication No. 2007-50106 and the like is configured to switch between a normal-light observation image and a special-light observation image, it is not possible to observe the two different images at the same time.

Thus, according to the invention described above, it is possible to provide an endoscope apparatus capable of coping with observation lights with various wavelengths and performing normal-light observation and special-light observation simultaneously while realizing downsizing.

Furthermore, by the embodiment of the invention described above, inventions configured as below can be obtained. That is:

(6) An image pickup unit including:
a first objective optical system;
a first image pickup device receiving a light flux having passed through the first objective optical system;
a second objective optical system arranged being provided with parallax relative to the first objective optical system;
a second image pickup device receiving a light flux having passed through the second objective optical system;
a first optical filter arranged between the first objective optical system and the first image pickup device;
a second optical filter constituted by a filter of a kind different from the first optical filter, the second optical filter being arranged between the second objective optical system and the second image pickup device; and
half prisms arranged between the first optical filter and the first image pickup device and between the second optical filter and the second image pickup device, the half prisms causing light fluxes having passed through the first optical filter and the second optical filter, respectively, to be reflected or pass through.

(7) The image pickup unit according to the item (6), wherein the first optical filter and the second optical filter are a pair of polarization filters whose polarization directions cross each other.

(8) The image pickup unit according to the item (7), wherein the half prisms are polarization beam splitters.

(9) An endoscope apparatus using the image pickup unit according to the item (6).

Here, among conventional endoscope apparatuses, various kinds of so-called 3D endoscope apparatuses which are configured so as to be able to acquire a three-dimensional image (a stereo image; a 3D image) by two image pickup devices being arranged side by side are proposed, for example, by Japanese Patent No. 4955840.

The 3D endoscope apparatuses disclosed by Japanese Patent No. 4955840 and the like are configured by arranging two independent image pickup units side by side at a distal end of an insertion portion.

In the endoscope apparatuses disclosed by Japanese Patent No. 4955840 and the like, however, there is a problem that, since the two image pickup units are arranged side by side, a configuration of the distal end portion of the insertion portion is large-scaled.

Thus, according to the above invention, by devising arrangement of the two image pickup devices to be arranged inside a distal end portion of an insertion portion in a 3D endoscope apparatus, it is possible to realize downsizing of the image pickup unit, and, therefore, it is possible to provide a 3D endoscope apparatus in which downsizing of the distal end portion of the insertion portion is realized.

Note that the present invention is not limited to the embodiments described above, and it is, of course, possible to make various changes and perform application within a range not departing from the spirit of the invention. Furthermore, the embodiments described above include inventions at various stages, and various inventions can be extracted by appropriate combinations among a plurality of disclosed constituent features. For example, even if some constituent features are deleted from all constituent features shown in one of the embodiments described above, a configuration from which the constituent features have been deleted can be extracted as an invention if the problem to be solved by the invention can be solved and the advantages of the invention can be obtained.

INDUSTRIAL APPLICABILITY

The present invention can be applied not only to an endoscope apparatus in a medical field but also to an endoscope apparatus in an industrial field.

What is claimed is:

1. An endoscope apparatus comprising:
   an image pickup unit comprising a first and at least second image sensor and an optical path dividing member for dividing a light beam entering from an objective lens into a first and at least second optical path and leading the first and at least second optical path to a respective first and at least second image sensor, wherein optical path lengths of the first and at least second optical path are different from one another; and
   a processor comprising hardware, the processor being configured to:
      acquire a first image from the first image sensor corresponding to the first optical path;
      acquire at least a second image from the at least second image sensor corresponding to the at least second optical path, the at least second optical path having a length greater than a length of the first optical path;
      comparing contrasts of the first and at least second images; and
      selecting one of the first and at least second images and outputting only an image signal from a corresponding first and at least second image sensor, on a basis of a result of the comparison.

2. The endoscope apparatus according to claim 1, wherein the difference among the contrasts is a difference among peak values of the contrasts of the first and at least second images based on respective image signals corresponding to the first and at least second images.

3. The endoscope apparatus according to claim 1, wherein the processor is further configured to control movement of a movable lens so that a difference among the contrasts of the first and at least second images outputted from the first and at least second image sensors, respectively, is largest, wherein a part of the objective lens is configured to be movable in an optical axis direction as the movable lens.

4. An endoscope apparatus comprising:
   an image pickup unit comprising a first and at least second image sensor and an optical path dividing member for dividing a light beam entering from an objective lens into a first and at least second optical path and leading the first and at least second optical path to a respective first and at least second image sensor, wherein optical path lengths of the first and at least second optical path are different from one another; and
   a processor comprising hardware, the processor being configured to:
      acquire a first image from the first image sensor corresponding to the first optical path;
      acquire at least a second image from the at least second image sensor corresponding to the at least second optical path, the at least second optical path having a length greater than a length of the first optical path;
      extract an image area with a high contrast from each of the first and at least second images; and
      generate a combined image signal having the image areas having the high contrast from each of the first and at least second images.

* * * * *